(12) United States Patent
Faller et al.

(10) Patent No.: US 10,624,667 B2
(45) Date of Patent: Apr. 21, 2020

(54) SYSTEM AND METHOD TO TRACK USAGE OF SURGICAL INSTRUMENT

(71) Applicant: Ethicon LLC, Guaynabo, PR (US)

(72) Inventors: Craig N. Faller, Batavia, OH (US); Benjamin D. Dickerson, Cincinnati, OH (US); Jeffrey L. Aldridge, Lebanon, OH (US); Jeffrey A. Bullock, Cincinnati, OH (US); Richard W. Timm, Cincinnati, OH (US); Ryan M. Asher, Cincinnati, OH (US); Timothy S. Holland, Cincinnati, OH (US); Craig T. Davis, Cincinnati, OH (US); Christina M. Hough, Cincinnati, OH (US); Cory G. Kimball, Hamilton, OH (US); Ashvani K. Madan, Mason, OH (US); David C. Yates, West Chester, OH (US); Shan Wan, Mason, OH (US); Jacob S. Gee, Cincinnati, OH (US); Joseph E. Hollo, Liberty Township, OH (US); Chad P. Boudreaux, Cincinnati, OH (US); John B. Schulte, West Chester, OH (US); Tylor C. Muhlenkamp, Cincinnati, OH (US); Brian D. Black, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 112 days.

(21) Appl. No.: 15/491,139

(22) Filed: Apr. 19, 2017

(65) Prior Publication Data
US 2017/0333073 A1 Nov. 23, 2017

Related U.S. Application Data

(60) Provisional application No. 62/339,151, filed on May 20, 2016.

(51) Int. Cl.
*A61B 17/32* (2006.01)
*A61B 18/04* (2006.01)
(Continued)

(52) U.S. Cl.
CPC ........... *A61B 17/320092* (2013.01); *A61B 17/320068* (2013.01); *A61B 18/04* (2013.01);
(Continued)

(58) Field of Classification Search
CPC ........ A61B 17/32; A61B 2017/320068; A61B 2017/320071; A61B 2017/320092;
(Continued)

(56) References Cited

U.S. PATENT DOCUMENTS

| 5,322,055 A | 6/1994 | Davison et al. |
|---|---|---|
| 5,873,873 A | 2/1999 | Smith et al. |

(Continued)

FOREIGN PATENT DOCUMENTS

| EP | 2 510 891 A1 | 10/2012 |
|---|---|---|
| EP | 2 923 653 A2 | 9/2015 |

OTHER PUBLICATIONS

International Search Report and Written Opinion dated Sep. 20, 2017 for Application No. PCT/US2017/032800, 11 pgs.
U.S. Appl. No. 62/339,151, filed May 20, 2016.

*Primary Examiner* — Ahmed M Farah
(74) *Attorney, Agent, or Firm* — Frost Brown Todd LLC

(57) ABSTRACT

Systems, devices, and methods are operable to track usage of a surgical instrument and modify the performance of the surgical instrument based on the prior usage of the surgical instrument. Some surgical instruments are designed to have a limited service life beginning at their first use, or a limit to their overall usage in order to ensure safe use of the sensitive instruments. However, a lack of ability to track usage characteristics when the instrument is separated from an (Continued)

external power supply allows for user abuse and avoidance of such safety mechanisms. Adding a battery or capacitor to the instrument may allow for an ability to track usage when the instrument is separated from an external power supply. Implementing special user prompts, device use ratios, and device use half-life upon powering down of an instrument may additionally be used to prevent circumvention of safety features.

20 Claims, 12 Drawing Sheets

(51) Int. Cl.
  *A61B 90/00* (2016.01)
  *A61N 7/02* (2006.01)
  *A61B 17/00* (2006.01)
  *A61B 18/12* (2006.01)
  *A61B 18/00* (2006.01)

(52) U.S. Cl.
  CPC ............... *A61B 90/08* (2016.02); *A61N 7/02* (2013.01); *A61B 18/12* (2013.01); *A61B 2017/0011* (2013.01); *A61B 2017/0046* (2013.01); *A61B 2017/00132* (2013.01); *A61B 2017/00424* (2013.01); *A61B 2017/00734* (2013.01); *A61B 2017/320094* (2017.08); *A61B 2017/320095* (2017.08); *A61B 2018/0063* (2013.01); *A61B 2018/00619* (2013.01); *A61B 2018/00678* (2013.01); *A61B 2018/1226* (2013.01); *A61B 2090/0803* (2016.02); *A61B 2090/0807* (2016.02); *A61B 2560/028* (2013.01); *A61B 2560/0266* (2013.01)

(58) Field of Classification Search
  CPC ....... A61B 2017/320093; A61B 2017/320094; A61B 2017/320095; A61B 2017/320097; A61B 2017/00017; A61B 2017/00106; A61B 2017/0011; A61B 2017/00132; A61B 2017/00137; A61B 2017/00199; A61B 2017/00681; A61B 2017/00734; A61B 2018/00571; A61B 2018/00577; A61B 2018/00589; A61B 2018/00595; A61B 2018/00601; A61B 2018/00607; A61B 2018/00619; A61B 2018/00625; A61B 2018/0063; A61B 90/08; A61B 2090/0803; A61B 2090/0804; A61B 2090/0805; A61B 2090/0806
  USPC .................................... 606/1, 130, 205–208
  See application file for complete search history.

(56) References Cited

U.S. PATENT DOCUMENTS

| | | | |
|---|---|---|---|
| 5,980,510 A | 11/1999 | Tsonton et al. | |
| 6,325,811 B1 | 12/2001 | Messerly | |
| 6,773,444 B2 | 8/2004 | Messerly | |
| 6,783,524 B2 | 8/2004 | Anderson et al. | |
| 7,074,179 B2 * | 7/2006 | Wang .................... | A61B 34/75 414/2 |
| 8,461,744 B2 | 6/2013 | Wiener et al. | |
| 8,591,536 B2 | 11/2013 | Robertson | |
| 8,623,027 B2 | 1/2014 | Price et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,333,025 B2 | 5/2016 | Monson et al. | |
| 9,393,037 B2 | 7/2016 | Olson et al. | |
| 9,402,647 B2 | 8/2016 | Kawashima et al. | |
| 9,913,680 B2 | 3/2018 | Voegele et al. | |
| 10,265,092 B2 * | 4/2019 | Rosa ................. | A61B 18/1445 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2011/0295269 A1 * | 12/2011 | Swensgard .......... | A61B 17/068 606/130 |
| 2014/0052154 A1 * | 2/2014 | Griffiths ................. | B25J 9/1633 606/130 |
| 2014/0367446 A1 * | 12/2014 | Ingmanson ...... | A61B 17/07207 227/175.2 |
| 2018/0049823 A1 * | 2/2018 | Shelton, IV .......... | A61B 34/30 |
| 2019/0314056 A1 * | 10/2019 | Brady ............ | A61B 17/320068 |

* cited by examiner

SYSTEM AND METHOD TO TRACK USAGE OF SURGICAL INSTRUMENT

PRIORITY

This non-provisional patent application claims the benefit of U.S. provisional patent application 62/339,151, filed May 20, 2016, the disclosure of which is hereby incorporated by reference in its entirety.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014 the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include an articulating shaft section. Examples of such ultrasonic surgical instruments are disclosed in U.S. Pub, No. 2014/0005701; entitled "Surgical Instruments with Articulating Shafts," published Jan. 2, 2014, issued as U.S. Pat. No. 9,393,037 on Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

As a result of the critical nature of procedures performed with surgical instruments, extremely tight tolerances may be required both for newly manufactured instruments as well as for reusable instruments that have previously been put into service. While a particular surgical instrument may meet or exceed a specification at the time of manufacture, its performance may degrade after several uses due to normal wear and tear, or due to expansion of parts as a result of heat sterilization between uses. While manufacturers of such a product may provide guidelines for a number of uses before an instrument should be disposed of, cost conscious end users may ignore such guidelines and create safety and usage issues for end users and patients.

While a variety of systems have been made and used for surgical device lifecycle management, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Overview of Exemplary Ultrasonic Surgical Instruments

Figure 1:
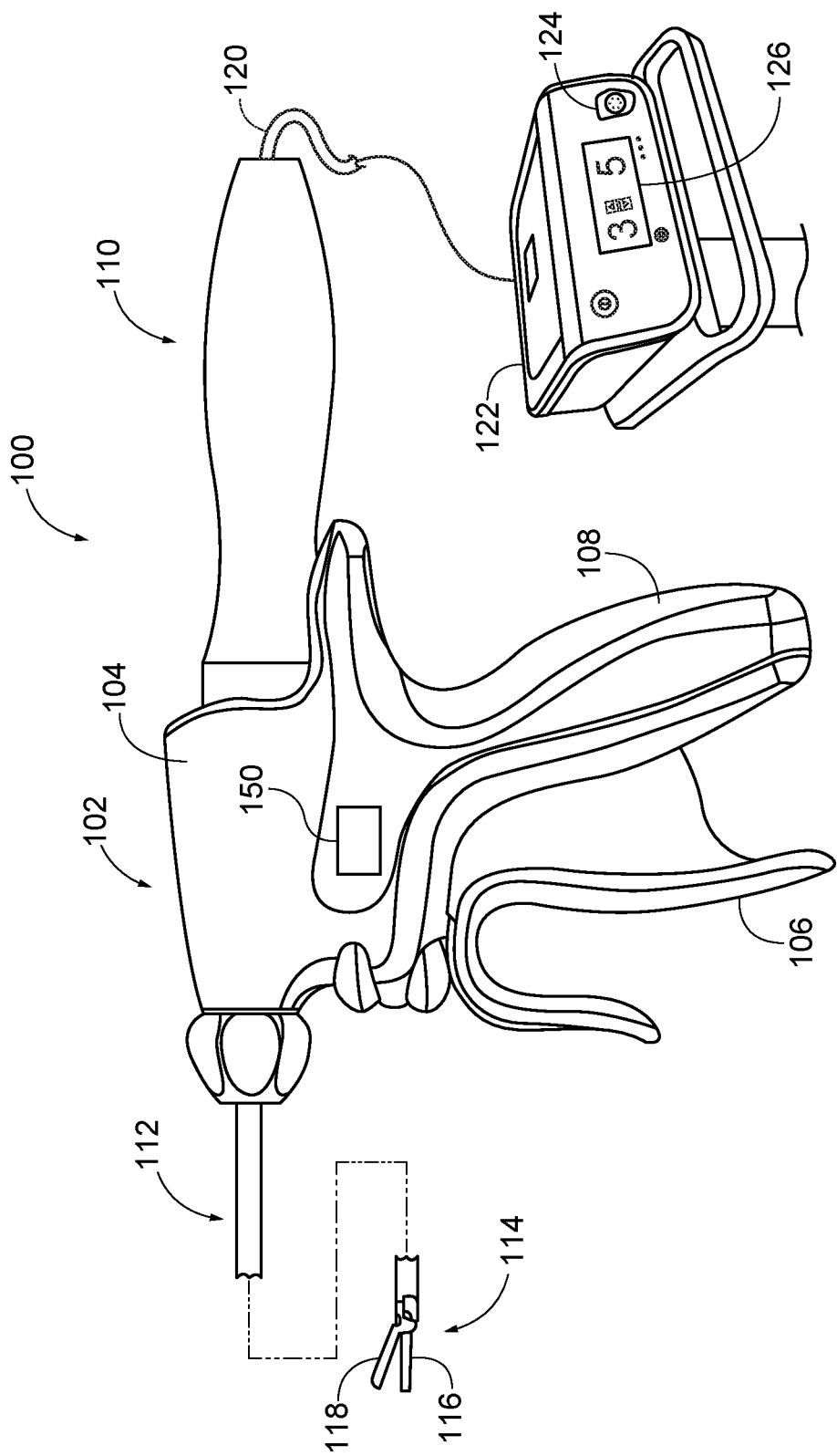
FIG. 1 depicts a schematic view of an exemplary ultrasonic surgical system.

FIG. 1 shows a side elevation view of an exemplary surgical instrument (100). Instrument (100) is operable to cut tissue and seal or weld tissue substantially simultaneously. It should also be understood that instrument (100) may have various structural and functional similarities with the HARMONIC ACE® Ultrasonic Shears. Furthermore, instrument (100) may have various structural and functional similarities with the devices taught in any of the other references that are cited and incorporated by reference herein.

Instrument (100) is configured to be used as a shears. Instrument (100) of this example comprises a handle assembly (102), a shaft assembly (112), and an end effector (114). Handle assembly (102) comprises a body (104) including a pistol grip. Handle assembly (102) also includes a trigger (106) that is pivotable toward and away from pistol grip (108). It should be understood, however, that various other suitable configurations may be used, including but not limited to a pencil-grip configuration or a scissor-grip configuration. An ultrasonic transducer assembly (110) extends proximally from body (104) of handle assembly (102). Transducer assembly (110) is coupled with generator (122) via a cable (120) connected to receptacle assembly (124), such that instrument (100) and generator (122) cooperate to form an ultrasonic surgical system. Transducer assembly (110) receives electrical power from generator (122) and converts that power into ultrasonic vibrations through piezoelectric elements.

Various suitable forms that generator (122) may take will be apparent to those of ordinary skill in the art in view of the teachings herein, and may include, for example, a fixed battery, a removable battery, an inductive power supply, or the like. By way of example only, generator (122) may comprise a GEN 11 or GEN 300 sold by Ethicon Endo-Surgery, Inc, of Cincinnati, Ohio. In addition or in the alternative, generator (122) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. Still other suitable forms that generator (122) may take, as well as various features and operabilities that generator (122) may provide, will be apparent to those of ordinary skill in the art in view of the teachings herein.

End effector (114) includes an ultrasonic blade (116) and a pivoting clamp arm (118). Clamp arm (118) is coupled with trigger (106) such that clamp arm (118) is pivotable toward ultrasonic blade (116) in response to pivoting of trigger (106) toward pistol grip (108); and such that clamp arm (118) is pivotable away from ultrasonic blade (116) in response to pivoting of trigger (106) away from pistol grip (108). Various suitable ways in which clamp arm (118) may be coupled with trigger (106) will be apparent to those of ordinary skill in the art in view of the teachings herein.

Blade (116) of the present example is operable to vibrate at ultrasonic frequencies in order to effectively cut through and seal tissue, particularly when the tissue is being compressed between clamp arm (118) and blade (116). Blade (116) is positioned at the distal end of an acoustic drivetrain. This acoustic drivetrain includes transducer assembly (110) and an acoustic waveguide (not shown) that extends through shaft assembly (112). Transducer assembly (110) includes a set of piezoelectric elements (not shown) that are located proximal to a horn (not shown) of the rigid acoustic waveguide. The piezoelectric discs are operable to convert electrical power into ultrasonic vibrations, which are then transmitted along the acoustic waveguide to blade (116) in accordance with known configurations and techniques. By way of example only, this portion of the acoustic drivetrain may be configured in accordance with the teachings of the various references that are cited herein. When ultrasonic blade (116) is in an activated state (i.e., vibrating ultrasonically), ultrasonic blade (116) is operable to effectively cut through and seal tissue, particularly when the tissue is being clamped between clamp arm (118) and ultrasonic blade (116).

While the following teachings are provided in the context of instrument (100), it should be understood that the following teachings may be readily applied in the contexts of various other kinds of instruments. By way of example only, the following teachings may be readily applied in the contexts of any of the instruments described in the various references cited herein. It should also be understood that the following teachings may be readily applied to instruments that are not ultrasonic surgical instruments, including but not limited to RE electrosurgical instruments, surgical staplers, and various other kinds of instruments. Other suitable contexts in which the following teachings may be applied will be apparent to those of ordinary skill in the art in view of the teachings herein.

II. Surgical Instrument Life Management Features

Some surgical instruments, such instrument (100) described above, may implement usage tracking and control features to enable manufacturers to have some control over the instrument after an owner or end-user takes possession of the instrument. With complex and sensitive surgical instruments being used in life saving medical procedures, it can become a serious safety issue if surgical instruments are overused, abused, or otherwise used outside of their intended purpose or safe operating specification. To reduce dangers relating to overuse and abuse of surgical instruments, surgical instruments may be configured to become fully or partially disabled after the occurrence of certain events. As an example, a surgical instrument (100) may have fragile components that operate under high physical stress such as an end effector (114) or transducer (110). With unlimited use, failure of these components may be all but inevitable, and may have harmful consequences if a failure occurs during a surgical procedure.

To prevent dangerous over-use, a surgical instrument (100) may contain an EEPROM (150) or other memory feature that is configured to track various data such as the total amount of time instrument (100) is connected to a generator (122), the total number of activations of a blade (116) or clamp arm (118), the total number of times an advanced feature such as adaptive tissue technology (ATT) is activated, average power produced by instrument (100), average current drawn by instrument (100), activation types, activation durations, or other data stemming from the use of the instrument (100) during a surgical procedure. To further the example, when various conditions have been met, such as when information stored on EEPROM (150) indicates that instrument (100) has been activated more than 50 times, EEPROM (150) contents may be modified to completely disable instrument (100) until such a time that it can be inspected or reconditioned and returned to service. By way of example only, EEPROM (150) may be read and/or re-written by generator (122). By way of further example, EEPROM (150) may be located in handle assembly (102) or elsewhere. While an EEPROM (150) is used in the present example, various other suitable kinds of memory features that may be used will be apparent to those of ordinary skill in the art in view of the teachings herein.

These configurations may be broadly referred to as instrument (100) life management configurations or features, with the particular conditional events and resulting instrument (100) configuration changes varying by particular embodiments. One such instrument (100) life management feature could be to exclusively pair a particular surgical instrument (100) with a particular generator (122) after the instrument (100) is powered by the generator for an amount of time that exceeds a certain threshold. For example, if a surgical instrument (100) is connected to a generator (122) for more than 10 hours, EEPROM (150) of the instrument (100), and, in some cases, a memory of the generator (122), may each be modified to store a unique identifier associated with the other. Whenever instrument (100) is connected to a given generator (122), that generator (122) will check EEPROM (150) of instrument (100) to determine if there is a unique generator identifier stored. If there is no unique identifier, instrument (100) will function with any generator (122) that it is connected to. If there is a unique identifier, instrument (100) will only function with the generator (122) that is uniquely identified by the identifier. This feature, which may be referred to as generator pairing, is intended to prevent a single instrument (100) from being used with many different generators (122) in an attempt to prevent any single generator (122) from gathering enough usage data to determine that the instrument (100) has exceeded a safe usage threshold, while still allowing an instrument (100) to be used in the ordinary course of a medical procedure, which may require that the instrument (100) be swapped out for another instrument (100), removed and cleaned, removed for troubleshooting, and the like. Generator's (122) ability to store generator identifiers could vary based upon desired capabilities, and could include, for example, permanent storage of identifiers, storage of a configurable number of recently used devices, storage of a unique identifier for a certain period of time, and other storage procedures.

Another instrument (100) life management feature could be to completely or partially disable an instrument (100) after the total time that the instrument (100) is plugged into any combination of generators (122) exceeds 12 hours. This feature may be referred to as a total powered time limitation, and may be tracked by constantly updating a time value stored on EEPROM (150) of the instrument (100), a memory of the generator (122), or both. Once the total powered time exceeds a threshold, such as 12 hours, EEPROM (150) or a generator (122) memory or both will be updated to store a piece of data indicating that the total powered time for the instrument (100) has been exceeded. Each time the instrument (100) is connected to a generator (122), this data is searched for and, if present, the instrument (100) will not function. This feature is intended to prevent overuse of the instrument (100) by circumventing its normal operations or using instrument (100) in unpredictable ways that may extend its allowed life. Limiting the total powered time may prevent a user from achieving indefinite use by attempting to circumvent generator (122) pairing.

Another instrument (100) life management feature could be a limitation on the number of times an instrument (100) could be plugged into a generator (122). This feature may be referred to as a total connection limitation, and may be tracked by incrementing a counter stored on EEPROM (150) of an instrument (100), a memory of generator (122), or both, each time the instrument (100) is connected to a generator (122). When this counter exceeds a certain limit, EEPROM (150) data may be modified to disable instrument (100) for subsequent connections. This feature is intended to prevent circumvention of safety features by connecting the instrument (100) only for very brief periods when it is needed, and keeping it unconnected from a power supply at all other times in order to prevent any usage data from being gathered or incremented on EEPROM (150). One or more of the above features may be implemented on surgical instruments (100) and generators (122) in order to prevent various circumventions of instrument (100) safety features.

III. Tracking Usage with a Battery or Capacitor

Despite the inclusion of instrument (100) life management features in an instrument (100), some surgical instruments, especially those lacking a passive disconnected power source, may have weaknesses in usage tracking that may be exploited to circumvent these usage-based safety features. Due to the lack of any persistent real time clock in some instruments (100) and generators (122), a user of instrument (100) may briefly plug instrument (100) into a generator (122), use instrument (100), and unplug instrument (100) from generator (122) multiple times during a medical procedure. In this way, the user may avoid total powered time and generator (122) pairing limitations, and may still extend the life of instrument (100) far beyond its intended use before total connection limitations may disable instrument (100). One way to address this unintended usage would be to add a persistent clock to a surgical instrument (100) or generator (122). However, a persistent clock would then require a constant power supply, and may require recharging of a battery, battery replacement, placement near electrical outlets, and other complications that may be costly and may impair usability.

Figure 2:
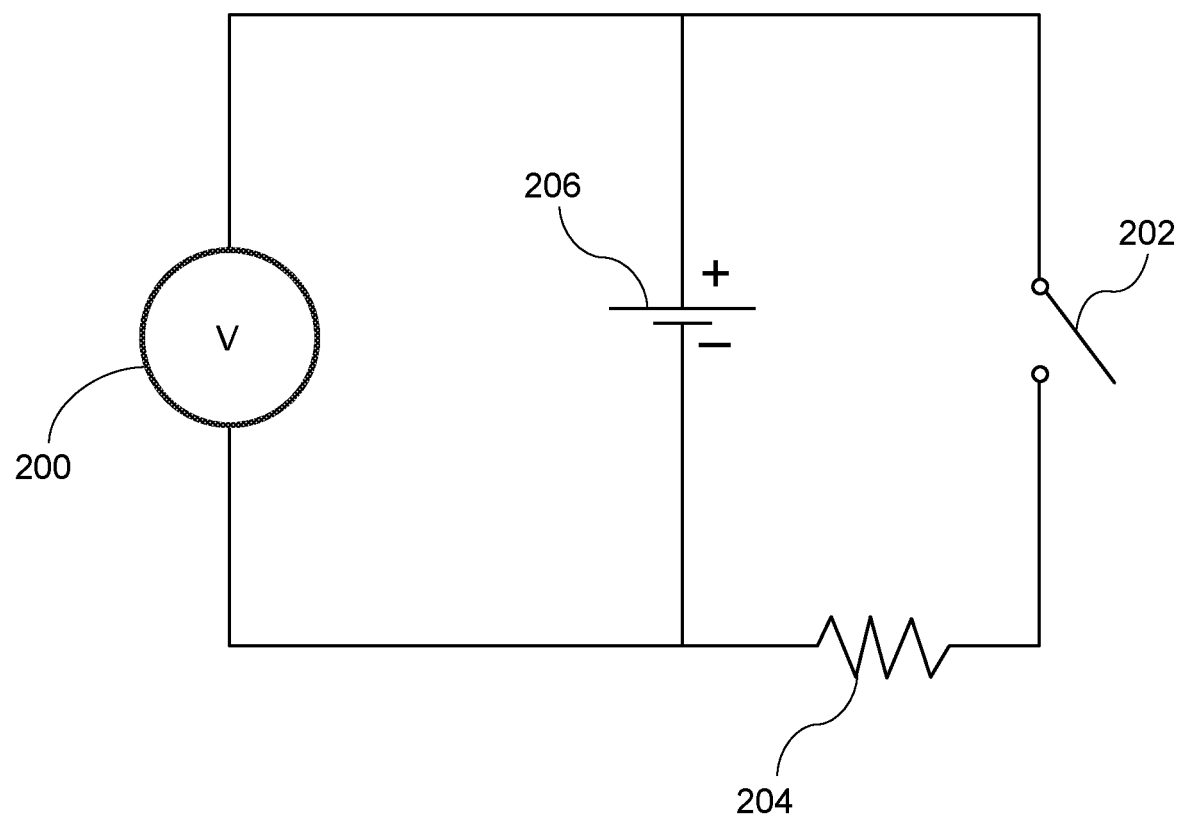
FIG. 2 depicts a schematic view of an exemplary circuit that may be incorporated into the system of FIG. 1, having a battery with a predictable discharge rate used to simulate a persistent clock.

One alternative to adding an integral real time clock is to add a single use battery placed in a circuit with a predictable rate of discharge. For example, FIG. 2 shows an exemplary circuit having a battery (206) with a predictable discharge rate to simulate a persistent clock. Such a circuit could be placed in an instrument (100) and configured so that, when connected to a generator (122), generator (122) would check voltage at a voltage indicator (200) in order to determine the current charge of a battery (206). Battery (206) could be charged to a known and measurable charge level at the time of installation, and would substantially maintain such a level while not in use. Also included in the circuit would be an activation switch (202) and a resistor (204). Switch (202) would be initially provided in an open state. However, switch (202) would be closed when instrument (100) is first coupled with generator (122). When switch (202) is closed, thereby closing the circuit, resistor (204) would begin to discharge battery (206) at a predictable rate. Switch (202) may comprise a one-way mechanical switch, an electrical switch, logic switch, or some other changeable state construct that may interface with an electrical circuit such that once switch (202) is first closed, switch (202) remains permanently closed. Switch (202) is thus activated or closed when instrument (100) is connected to a generator (122) and remains closed even after instrument (100) is disconnected from generator (122). Various suitable ways in which switch (202) may be configured will be apparent to those of ordinary skill in the art in view of the teachings herein.

Figure 3:
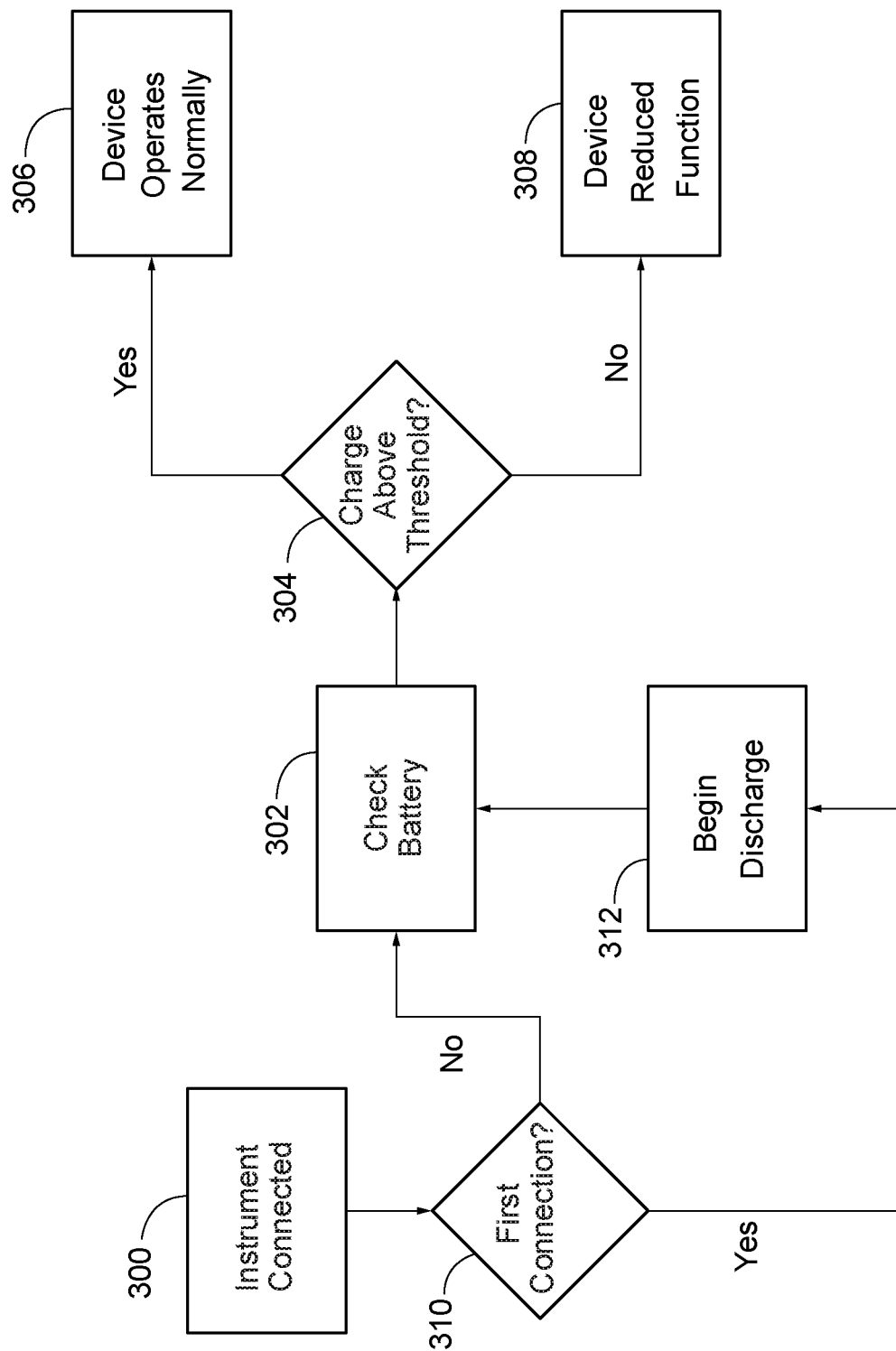
FIG. 3 depicts a flow chart showing an exemplary set of steps that may be performed to simulate a persistent clock for the system of FIG. 1.

The net result of the above described circuit is a battery (206) with known charge that discharges at a predictable rate after the first time an instrument (100) is connected to a generator (122). FIG. 3 shows an exemplary set of steps that may be performed with a generator (122) and instrument (100) using the circuit shown in FIG. 2. When instrument (100) is first connected (block 300) to generator (122), if it is the first time the instrument (100) has been connected to a generator (block 310), battery (206) will begin to discharge as a result of switch (202) being activated or closed. After battery (206) discharge begins (block 312), or if this is not the first connection (block 310), generator (122) determines (block 302) the current charge remaining in the battery (206) by checking voltage indicator (200). If this determination indicates that battery (206) charge is above a certain threshold (block 304), then generator (122) may operate instrument (100) normally (block 306). If the determination indicates that the battery (206) charge is below a certain threshold (block 304), then generator (122) may operate instrument (100) at a reduced functionality, such as disabling certain features or reducing maximum operational performance (block 308). In some cases, generator (122) may reduce the instrument (100) function entirely, either by not providing the instrument (100) power, or by modifying the contents of the instrument (100) EEPROM (150) to place it into reduced operation state, or both, when detecting that the battery (206) charge is below a certain threshold. Since the initial charge of battery (206) and the resistance value of resistor (204) are known and controllable, resulting a predictable discharge rate for battery (206), the present charge level of battery (206) can be used as an indication of how much time has passed since instrument (100) was first connected to a generator (122) and causing switch (202) to close and begin battery (206) discharge. This operation of switch (202) could be achieved with a true standalone switch with an over-center closure that stays closed once switched for the first time. In another version, the resistor (204) itself may be part of the switch (202) function, with the resistor (204) being translated physically into the circuit and completing the circuit upon a first connection.

By varying the beginning charge of battery (206) and the resistance of resistor (204), battery (206) can be configured to discharge from an initial charge to a depleted charge within a desired time frame, which, as an example only, may be approximately 4-12 hours. This allows instrument (100) to have a strictly enforced lifespan, beginning from the first time a connection is made with generator (122). This lifespan may be long enough to allow a lengthy surgical procedure to be completed, but short enough to greatly reduce the likelihood of overuse or abuse of instrument (100). Implementing a battery (206) in this way to simulate a persistent clock avoids the need for replacing or recharging batteries, as the battery in the circuit described above is intended to be a one-time discharge.

While resistor (204) is used in the foregoing example, any other suitable component(s) may be used as a load to discharge battery (206) at a predetermined rate. Various suitable alternative discharge load features will be apparent to those of ordinary skill in the art in view of the teachings herein. For example, one alternative could be to include a light emitting diode (LED) or other simple light source in place of resistor (204). This could be placed within the body of instrument (100) so that light emitted by the LED is not visible, or could be placed on the exterior of instrument (100) and provide a visible indicator of whether battery (206) still has a charge sufficient to light the LED, which could also serve as an indicator that battery (206) still has sufficient charge to allow instrument (100) to function. As an additional alternative example, an electric micro motor or a vibration motor could be used instead of resistor (204), so that battery (206) could discharge at a predetermine rate as a result of the micro motor or vibration motor's operation. Yet another alternative example could be to include a simple timer element configured to countdown until a time of expiration, which could serve a dual purpose of providing both a countdown until expiration as well as a predictable rate of battery discharge, which could provide a useful redundancy for determining instrument (100) expiration despite a user's attempt to recharge battery (206). Other simple components or circuits could be used in place of or in addition to resistor (204), including but not limited to constant current sinks, various types of transmitters and receivers, an audio device such as a speaker, or other devices that might consume and convert into a different form the energy stored in a battery.

Figure 4:
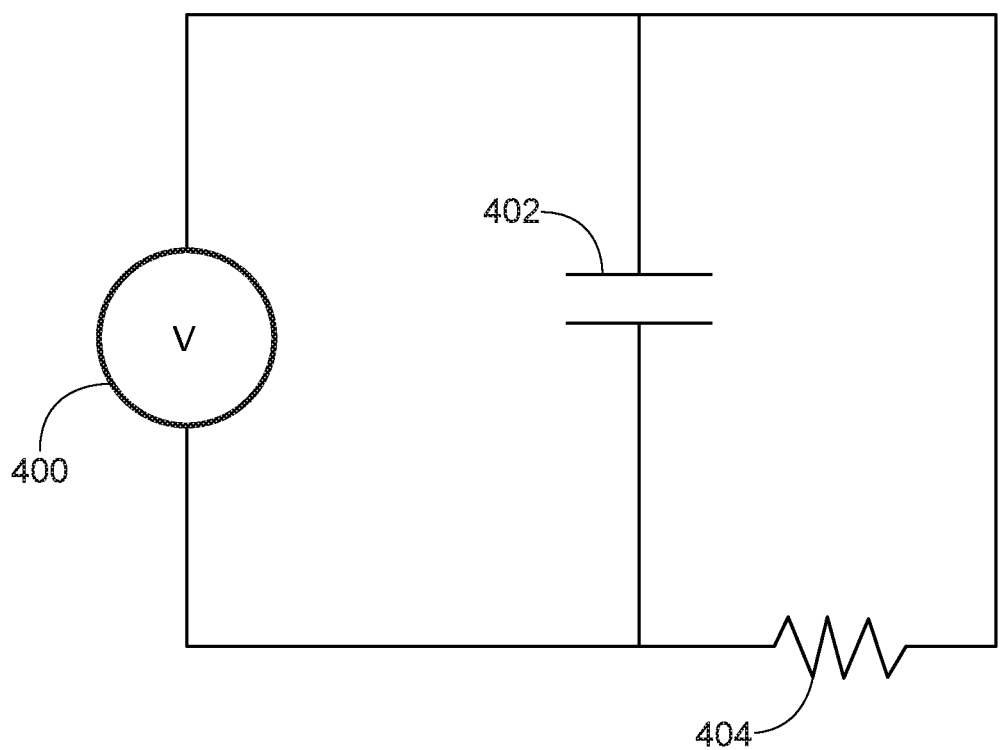
FIG. 4 depicts a schematic view of another exemplary circuit that may be incorporated into the system of FIG. 1, having a capacitor with a predictable discharge rate used to simulate a persistent clock.

Another version of surgical instrument (100) may use a capacitor instead of a battery (206) to simulate a persistent clock for instrument (100) life management purposes. FIG. 4 shows an exemplary circuit having a voltage indicator (400), a capacitor (402), and a resistor (404) that could be placed in an instrument (100). Such a configuration functions similarly to the circuit of FIG. 2, with a capacitor (402) that can be charged to a desired level upon connection of instrument (100) to generator (122). Once charged to an initial level, the charge stored by capacitor (402) will degrade at a predictable rate due to the presence of resistor (404) in the circuit. Periodically, or upon re-connection with a generator (122), the circuit voltage will be sampled at voltage indicator (400) and used to determine the remaining charge in capacitor (402) to provide an indication of elapsed time since instrument (100) was first connected to a generator (122) for a sufficient time period to charge capacitor (402) to the initial charge level. It should be appreciated that, while FIG. 4 shows capacitor (402) as a permanent feature of the circuit, it could function similarly to the switching mechanism of FIG. 2. For example, the capacitor may be fully charged initially, and may be placed into the circuit as part of a physical translation upon a first connection.

While resistor (404) is used in the foregoing example, any other suitable component(s) may be used as a load to discharge capacitor (402) at a predetermined rate. Various suitable alternative discharge load features will be apparent to those of ordinary skill in the art in view of the teachings herein. As with the resistor (204) of FIG. 2, resistor (404) could be replaced with or used in conjunction with an LED, a micro motor or haptic motor, a current sink, transmitter, receiver, speaker, timer, or other device or component that can predictably consume charge from capacitor (402).

Figure 12:
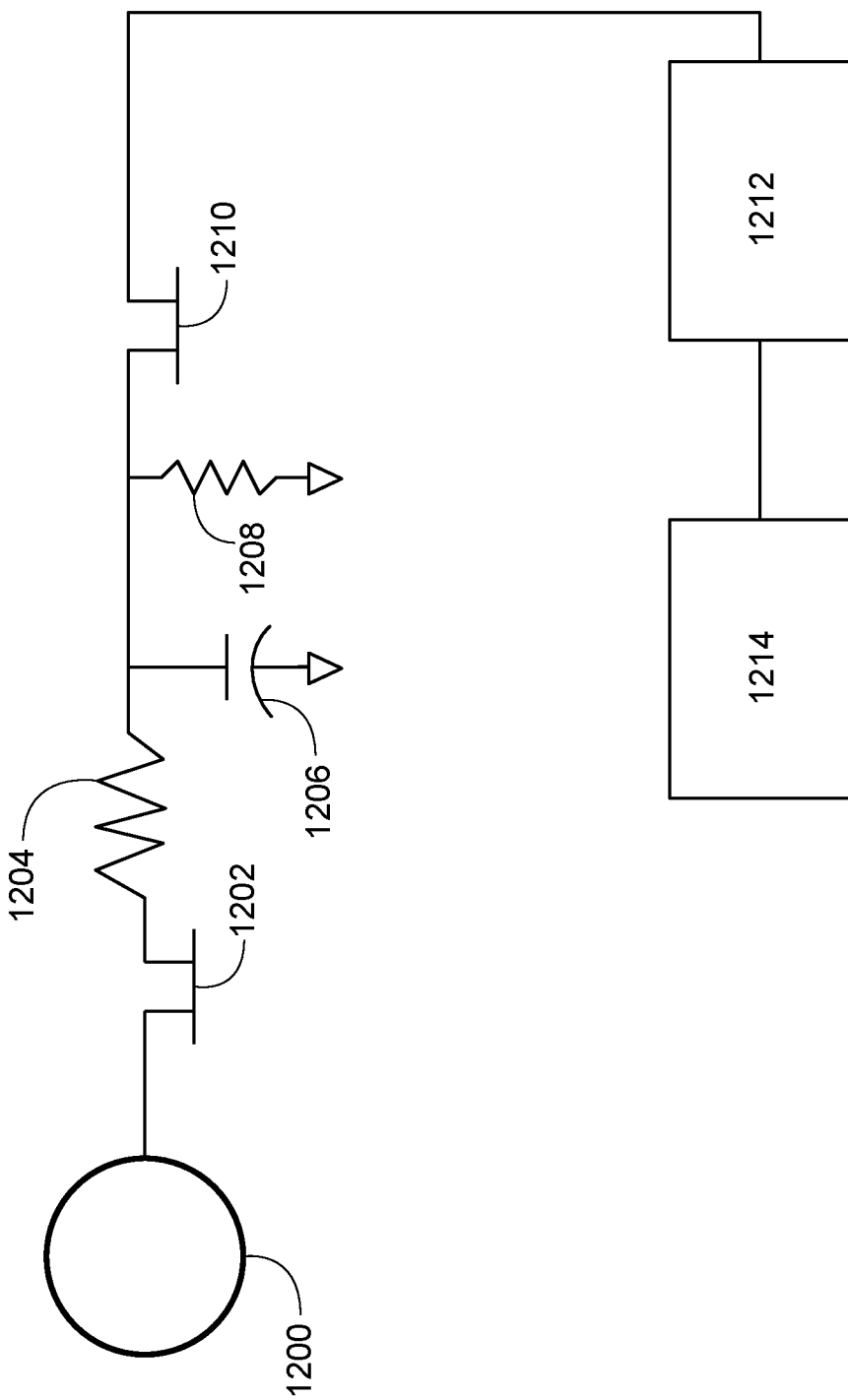
FIG. 12 depicts a schematic view of another exemplary circuit that may be incorporated into the system of FIG. 1, having a capacitor with a predictable discharge rate used to simulate a persistent clock.

Other circuit designs that may support a chargeable capacitor with predictable discharge will be apparent to one of ordinary skill in the art in light of the disclosure herein. For example, FIG. 12 shows a diagram of a circuit having a timing capacitor (1206) that may be charged upon a first connection of instrument (100) with generator (122), and then predictably discharge thereafter. A power source (1200) (e.g., within generator (122)) provides an approximate 5V, 5 mA charge at a charging point (1202). A resistor (1204) controls the flow of current to a timing capacitor (1206) to allow it to reach full capacitance shortly after a first connection to power source (1200). A second resistor (1208) provides a predictable discharge rate of capacitor (1206) after power source (1200) (e.g., generator (122)) is removed from the circuit. The capacitance of capacitor (1206) and the resistance of resistor (1208) may be varied to provide a variable number of minutes or hours of capacitance discharge, with the entire circuit being disabled when capacitor (1206) discharges below a configured threshold after the initial charge. A capacitor charge read point (1210) may be used to detect the current charge of capacitor (1206) to determine whether capacitor (1206) has reached a maximum charge at a first connection; and to determine whether the current charge of capacitor (1206) is above a threshold to allow normal operation. An analog to digital converter (1212) converts the voltage of timing capacitor (1206) into a digital format, which is transmitted to circuitry (1214) of instrument (100). Circuitry (1214) can analyze the digitized information on the voltage of timing capacitor (1206) to determine if it is above or below a configured threshold. In some alternative versions, circuitry (1214) is incorporated into generator (122) rather than instrument (100).

Figure 5:
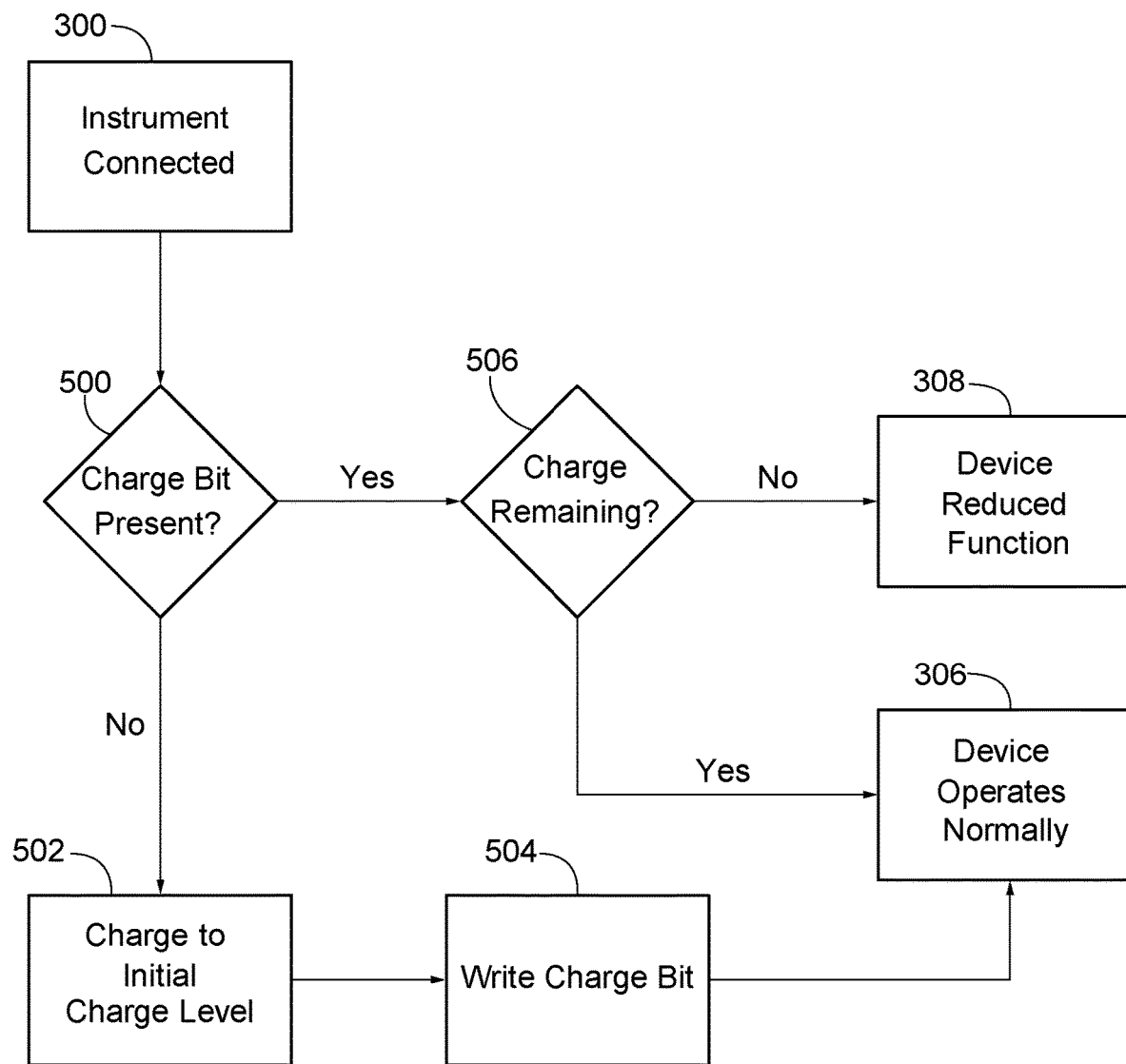
FIG. 5 depicts a flow chart showing an exemplary set of steps that may be performed to simulate a persistent clock for the system of FIG. 1.

FIG. 5 shows an exemplary set of steps that could be performed with the circuit of FIG. 4 in order to simulate a persistent clock. When instrument (100) is connected to generator (122), generator (122), instrument (100), or both will determine if a charge bit is present (block 500) on EEPROM (150) of instrument (100) or a memory of generator (122), or both. The charge bit may be a set of bits, bytes, or other data storage type that may be written to a memory to indicate that capacitor (402) has received an initial charge; and may also indicate additional information such as the initial charge level, the time required for complete discharge, and any other information available to generator (122) or instrument (100) at the time of connection such as software versions, owner information, location information or GPS information, and the like.

Upon a first connection of instrument (100) to a generator (124 the charge bit will not be present (block 500) in any EEPROM (150) or memory, and generator (122) will charge (block 502) capacitor (402) to a configured initial charge level and then write (block 504) the charge bit to EEPROM (150), a memory, or both to indicate that capacitor (402) received its initial charge. Thereafter, instrument (TOO) may operate normally (block 306) for a period of time, such as the time it remains connected to generator (122) or until capacitor (402) is fully discharged. If, after connection (block 300), the charge bit is determined to be present (block 500), generator (122) or instrument (100) or both will determine the charge remaining in capacitor (402), and if the charge remaining exceeds a threshold (block 506) indicating that instrument (100) is still within a usable life since its first connection and charging, instrument (100) will operate normally. If there is no charge remaining (block 506), or the charge falls below a certain threshold indicating that instrument (100) is outside of its usable life, instrument (100) may operate at a reduced function or may be disabled completely (block 308).

As with the example that incorporates a battery (206), the initial capacitor (402) charge and resistor (404) resistance may be varied to give instrument (100) a predictable lifespan after the first connection with a generator (122), such that capacitor (402) will quickly charge upon connection between instrument (100) and generator (122). Capacitor (402) will then completely degrade to the point where capacitor (402) will report no charge or no substantial charge (block 506) and result in instrument (100) becoming fully or partially inoperable (block 308) after a period of time that may range from about four to about fourteen hours. This example may have some advantages over the example shown in FIGS. 2-3, in that capacitor (402) may be simpler, more cost effective, or more durable than battery (206); and may result in a longer post-production shelf life since capacitor (402) has no charge upon first being produced and is only charged upon a first connection.

One variation of using a capacitor (402) or battery (206) to simulate a persistent clock would be to include a time tracking circuit in addition to a battery (206) or capacitor (402). In this manner a pre-charged battery (206), or a battery (206) or capacitor (402) that is charged upon connection between instrument (100) and generator (122), could provide a one-time reservoir of current to operate a time tracking circuit for between about four to fourteen hours and, when a configured elapsed time has been reached, write data to an EEPROM (150) or memory, or both, to indicate that instrument (100) is outside of its usable life.

Another variation on the above may be to include a circuit or mechanical component that provides a predictable and detectable change in some physical property that begins upon a connection of instrument (100) with a generator (122) instead of relying on a predictable change in voltage and charge level of a battery (206) or capacitor (402). This could include, for example, a predictable chemical reaction that begins upon connection, such as the release by mechanical means of a corrosive agent that over a predictable period of time eventually destroys a current carrying circuit or fuse; a release of a chemical that predictably changes the optical, resistive, capacitive, or similar properties of a sensor over time; or some other feature that relies on mechanical and/or chemical component to alter a state of instrument (100) after passage of a certain period of time following the initial coupling of instrument (100) with generator (122).

Another variation on the use of a capacitor (402) that is predictably discharged by a resistor (404) would be to use a high quality film capacitor instead of a capacitor (402) and resistor (404). A high quality film capacitor could be chosen based on low or predictable self-discharge characteristics. The high quality film capacitor could be charged upon initial connection similarly to the above described capacitor (402). The high quality film capacitor could be embedded in instrument (100) where it not visible or easily reachable, but where the use of a cleaning solution would expose the film capacitor to a conductive solution and cause it to fully or partially discharge when the instrument (100) is cleaned or sanitized after use. Upon a subsequent connection to a generator (122), a capacitor charge level that indicates instrument (100) has been exposed to a conductive cleaning solution can be used to fully or partially disable instrument (100) (block 308).

Another variation on the use of a capacitor (402) would be configure a capacitor (402) initial charge and resistor resistance (404) so that capacitor (402) is fully discharged between about five minutes and about twenty-five minutes after instrument (100) being disconnected from a generator (122); but while instrument (100) is connected to generator (122), capacitor (402) would always charge back to its initial charge level. The period of five to twenty-five minutes would allow for a user to disconnect instrument (100) for troubleshooting, brief cleaning, or to use a different instrument (TOO) with generator (122), but after such a period elapsed instrument (100) could be fully or partially disabled (block 308). In effect, an instrument (100) would maintain a high charge in capacitor (402) during constant use or during use with brief periods of disconnection; but once instrument (100) was disconnected from generator (122) for an extended period of time, such as at the end of a surgical procedure, capacitor (402) would discharge and write data to EEPROM (150) partially or fully disabling instrument (100) (block 308).

Figure 6:
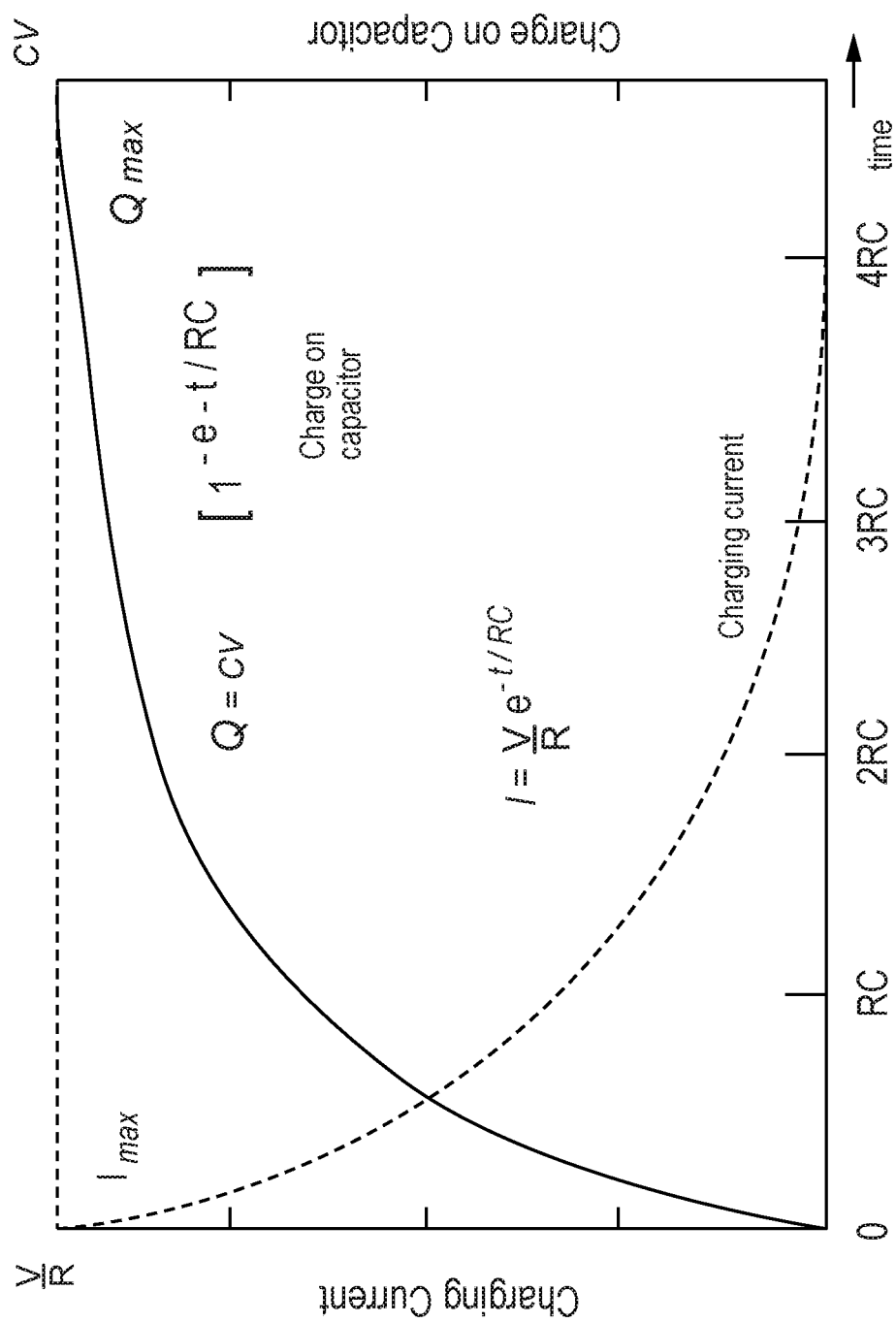
FIG. 6 depicts a graph showing a basic resistor-capacitor discharge model.
Figure 7:
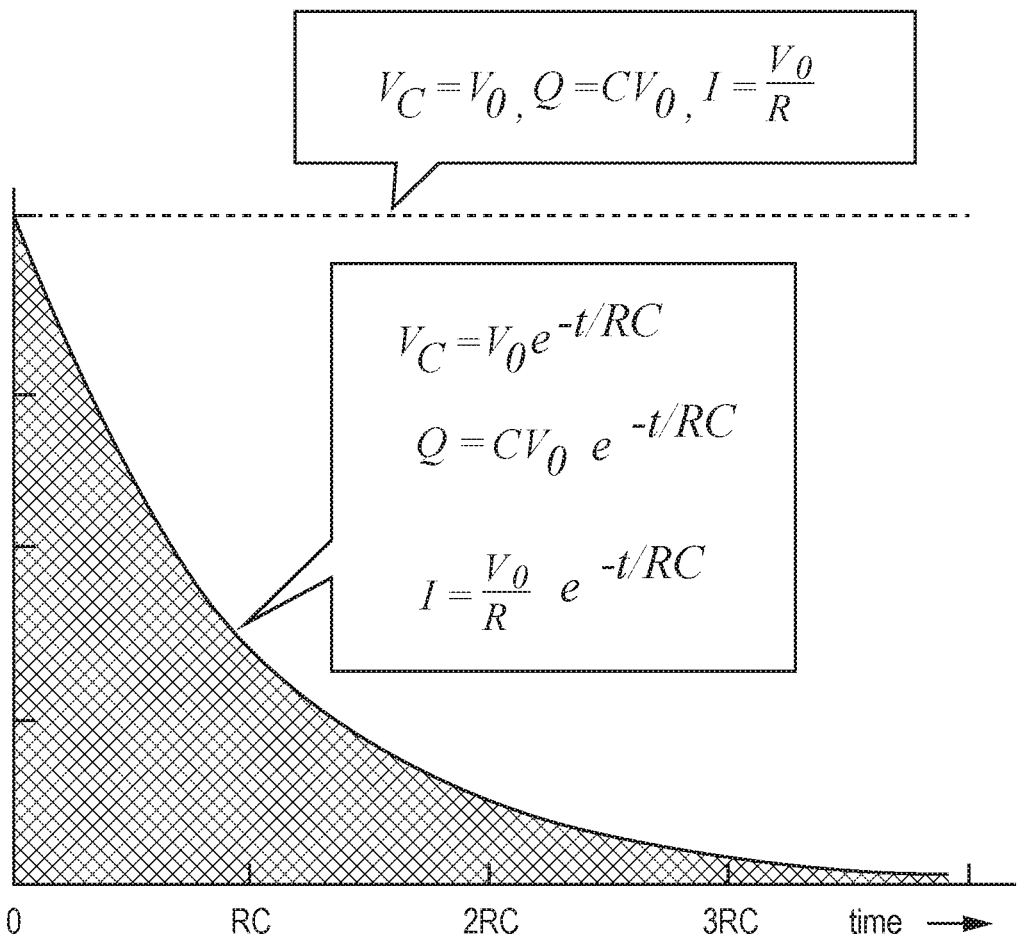
FIG. 7 depicts a graph showing a subset portion of a basic resistor-capacitor discharge model.

Capacitor (402) and resistor (404) may be implemented in a variety of ways in order to provide a particular desired life span for instrument (100). Voltage decay in a resistor-capacitor circuit is modeled with an exponential curve. The response of the decay is related to the amount of charge in the capacitor and the dissipative load associated with the capacitor's construction as well as external circuitry that are intended to either discharge the capacitor measure its voltage. FIG. 6 shows a basic resistor-capacitor discharge model, where Q is charge in Coulombs, V is measured voltage, I is current, R is resistance, C is capacitance in Farads, and t is time in seconds. FIG. 7 shows an isolated portion of the model of FIG. 6, which graphs the equation Vc=Q/C=IR. The time constant of a resistor-capacitor system is 1/RC. This means that the capacitor is charged or discharged at approximately 63% in the time of 1/RC seconds. Since the response is exponential, it takes several time constants before the capacitor is considered fully charged or discharged. In theory, the capacitor is never fully charged or discharged since the response curves asymptotically approach infinity. As a result, in order to achieve the desired charge and discharge times, capacitor size, charge time, resistor resistance, and voltage measurement may be varied.

For instance, according to the examples discussed above, discharge times for a capacitor (402) may vary from about five minutes, to more than ten hours. Ignoring variations in capacitor (402) that would affect the charge accumulated, such as manufacturing tolerances and variances, a capacitor (402) may be charged to about 5V from a current of about 5 mA, to keep maximum measured voltage within a reasonable range for sensitive circuitry and voltages and currents easily available to instrument (100) and generator (122). This example also assumes no substantial self-discharge of capacitor (402), which may be managed in real world versions by selection of materials, connections, insulations, and removal of contaminants to achieve the desired result. Voltage measurements may be taken only briefly, in order to minimize discharge of capacitor (402) as a result of measurement. With the assumptions above. Table 1 shows merely illustrative examples of voltage and current across several time constants for 5V on capacitor (402) and a 10M Ohm dissipative resistance and 0.25V threshold, which represents a 95% discharge and 3 time constants, using the equation Vc=Voe(t/RC), or c=(ln Vo/ln Vc)*(−t/R). Table 2 shows exemplary capacitance values that might be appropriate within this example to achieve specific discharge times.

TABLE 1

Voltage and Current Across Time Constants

| Time Constant | RC Value | Percentage of Max Voltage | Percentage of Max Current |
|---|---|---|---|
| 0.5 | 0.5T = 0.5RC | 39.3% | 60.7% |
| 0.7 | 0.7T = 0.7RC | 50.3% | 49.7% |
| 1.0 | 1T = 1RC | 63.2% | 36.8% |
| 2.0 | 2T = 2RC | 86.5% | 13.5% |
| 3.0 | 3T = 3RC | 95% | 5% |
| 4.0 | 4T = 4RC | 98.2% | 1.8% |
| 5.0 | 5T = 5RC | 99.3% | 0.7% |

TABLE 2

Capacitor Value to Achieve Desired Discharge Time

| Discharge Time in Minutes | Discharge Time in Seconds | Capacitor Value, uF |
|---|---|---|
| 1 | 60 | 7 |
| 2 | 120 | 14 |
| 5 | 300 | 35 |
| 600 | 36,000 | 250,000 |

Power to manage charging capacitor (402), and also to operate measurement and reporting circuitry, may be provided by generator (122). In order to rapidly charge capacitor (402) with current provided by generator (122), which may be about 5 mA, the smaller values of capacitance from Table 2 may be charged with a simple limiting resistor of 1 k ohms that keeps a 5V source limited to 5 mA. The capacitor (402) for the 1, 2, and 5-minute discharge are charged with a half a second. The capacitor (402) for 10-hour discharge, with a 5 mA constant current, reaches a 5V charge in about 250 seconds. Suitable variations on the concepts above will be apparent to one of ordinary skill in the art in light of the disclosure herein.

IV. User Interface Improvements to Track Usage

Figure 8:
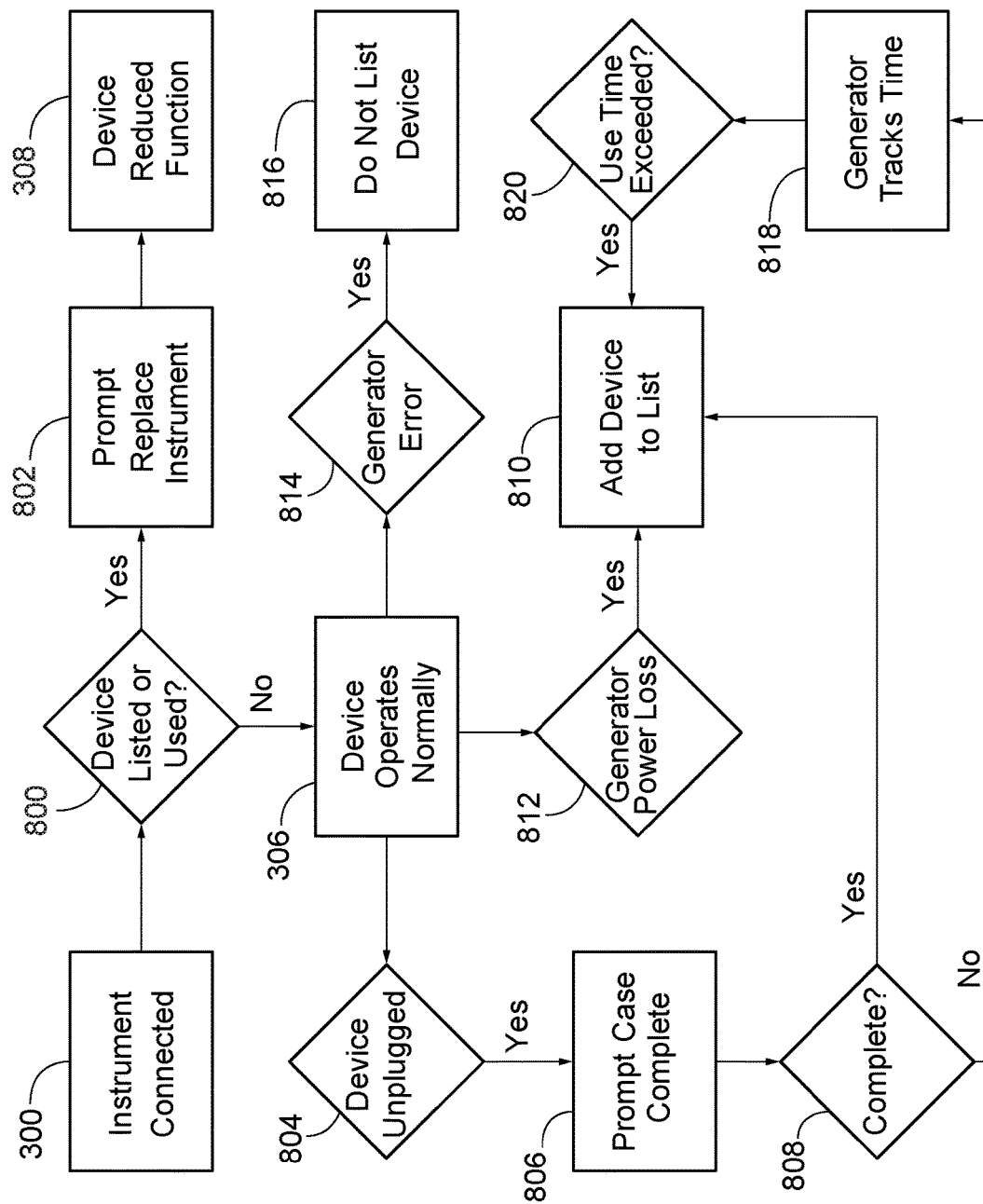
FIG. 8 depicts a flow chart showing an exemplary set of steps that may be performed to prompt a user for additional feedback that may be used to manage device life.

User interface improvements for controls and displays available on generator (122) may be combined with other instrument (100) life management features to provide additional user feedback and inputs to better track instrument (100) usage and implement instrument (100) life management features. FIG. 8 shows an exemplary set of steps that may be performed with a generator (122) and instrument (100) to prompt and receive additional user feedback to better manage instrument (100) life and usage. When instrument (100) is connected to generator (122), generator (122) checks EEPROM (150) of instrument (100) and retrieves a unique instrument (100) identifier that it compares to a list of instruments (100) stored on a memory of generator (122), and may also check EEPROM (150) of instrument (100) for data indicating that instrument (100) has been used with a generator previously. If the connected instrument (100) is already listed for generator (122) or has been used (block 800) with another generator, generator (122) will prompt (block 802) the user with a "replace instrument" message and partially or fully disable (block 308) instrument (100) by modifying EEPROM (150) of instrument (100). If instrument (100) is not listed (block 800), instrument (100) will operate normally (block 306) until a subsequent event occurs.

If instrument (100) is unplugged from generator (122), generator (122) will display a prompt (block 806) to the user inquiring as to whether the case, or medical procedure, is complete. If the user indicates that the case is complete (block 808), the unique identifier associated with the used instrument (100) will be added to the listing of instruments (100) in generator (122), so that the same instrument (100), if connected again in the future (block 300), will be located on the listing of instruments (100) (block 800). If the user instead indicates that the case is not complete (block 808), the generator (122) will remain powered on and continue to track instrument (100) usage time (block 818). When instrument usage time tracked (block 818) by generator (122) exceeds (block 820) instrument (100) allowed use time, instrument (100) will be added to the listing of instruments in generator (122) and will be identified (block 800) as being listed in subsequent connections. In a different scenario, if generator (122) loses power (block 812), indicating that the user may be attempting to circumvent unplugging instrument (122) (block 804), generator (122) will immediately add instrument (122) to the list (block 810) before generator (122) completely powers down. In another scenario, if generator (122) reports any sort of error (block 816) that may indicate a legitimate need to power down generator (122), generator (122) will power down based upon a user input without adding instrument (100) to the generator list (block 816).

V. External Usage Tracking Device

An external usage tracking device could also be used in conjunction with an instrument (100) and generator (122) to provide persistent time tracking of time intervals between a first connection of instrument (100) to a generator (122) and subsequent connections between instrument (100) and generator (122). An external usage tracking device could be in the form of a USB fob or stick that attaches to a USB port of generator (122), an adaptor that attaches inline between generator (122) and instrument (100), or the like; and may contain a processor, memory, and battery, and be configured to track the passage of time whether connected to a generator (122) or not. This could be achieved, for example, by tracking clock time, or by tracking the passage of seconds from an arbitrary time and relating each instrument (100) that the external usage tracking device communicates with to a point on the arbitrary timeline.

Figure 9:
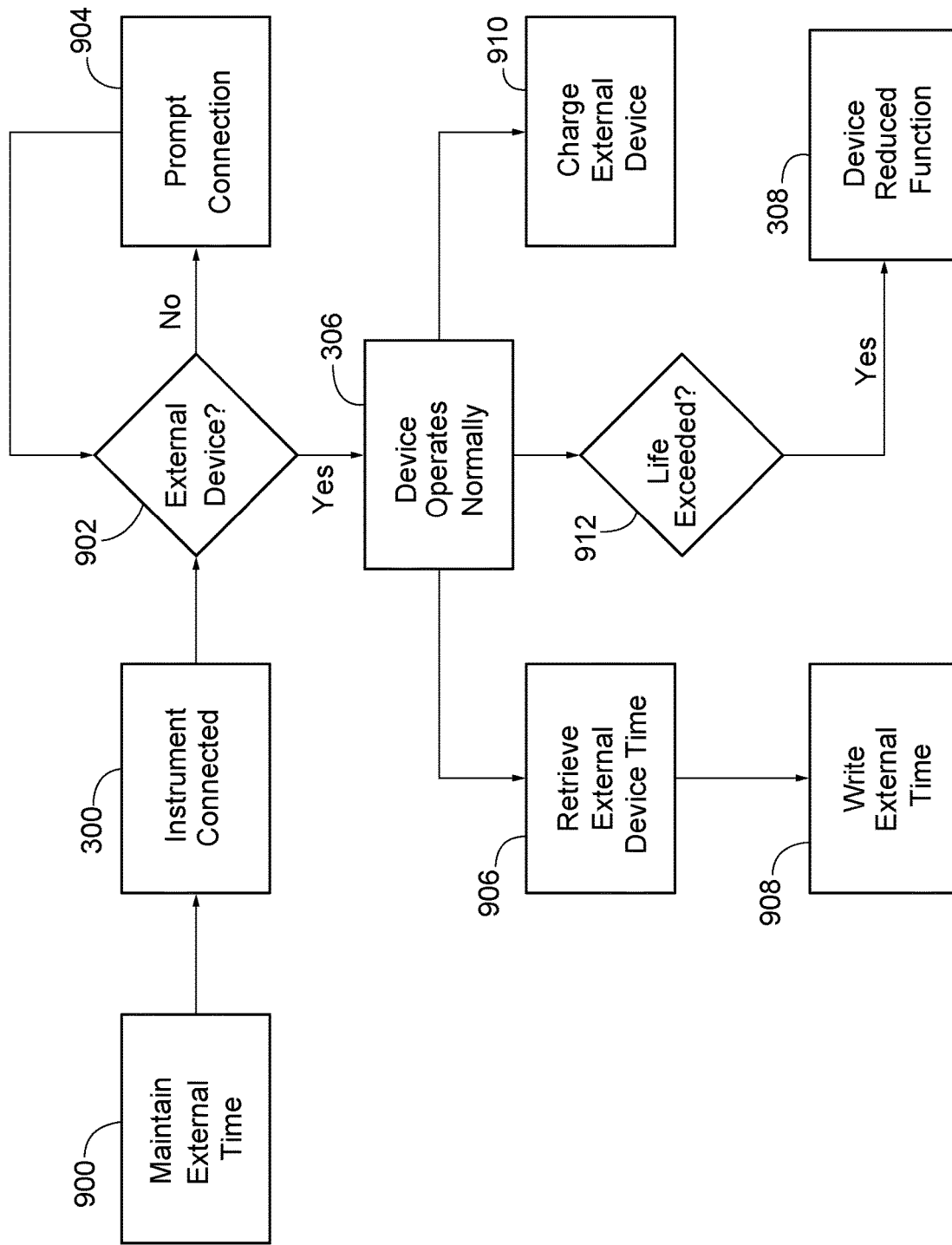
FIG. 9 depicts a flow chart showing an exemplary set of steps that may be performed with an external device to provide a persistent clock with an external device.

FIG. 9 shows a set of exemplary steps that may be performed with an external device, an instrument (100), and a generator (122). When the external device first receives power (e.g., from generator (122) or from another source), the external device will begin to maintain a time externally (block 900) whether it is connected to generator (122) or not. When an instrument (100) is connected to generator (122), generator (122) will determine whether the external device is connected to generator (122) (block 902). If the external device is not connected to generator (122) (block 902), generator (122) will prompt the user to connect the external device to generator (122) (block 904) and take no further action until the external device is determined to be connected to generator (122) (block 902). Once the external device is connected to generator (122), instrument (100) will operate normally (block 306) and generator (122) will charge the battery of the external device (block 910). Generator (122) may also retrieve a time indicator from the external device (block 906) and write the external time to EEPROM (150) of instrument (100) (block 908) to provide an instrument (100) life starting point, or subsequent use point. If, based upon external time stamps written to EEPROM (150), generator (122) or instrument (100) determine that, as a result of elapsed time, usable life has been exceeded for instrument (100) (block 912), EEPROM (150) of instrument (100) will be modified to cause instrument (100) to operate at a reduced or disabled function (block 308).

The external device could, in some versions, include wireless internet capabilities, Bluetooth capabilities, or other wireless or wired connections that could facilitate sharing of data between generator (122) and instrument (100) and one or more remote computers or servers, etc. This could allow valuable usage data to be pulled from sources that are typically not connected to a network and transmitted to a remote server for further use or study. This could additionally allow for software updates for generators (122) and instruments (100) to be disseminated through typical routine usage of generators (122) and instruments (100), rather than requiring special service by technicians or users.

VI. Tracking Device Life by Ratio of Known Usage

Figure 10:
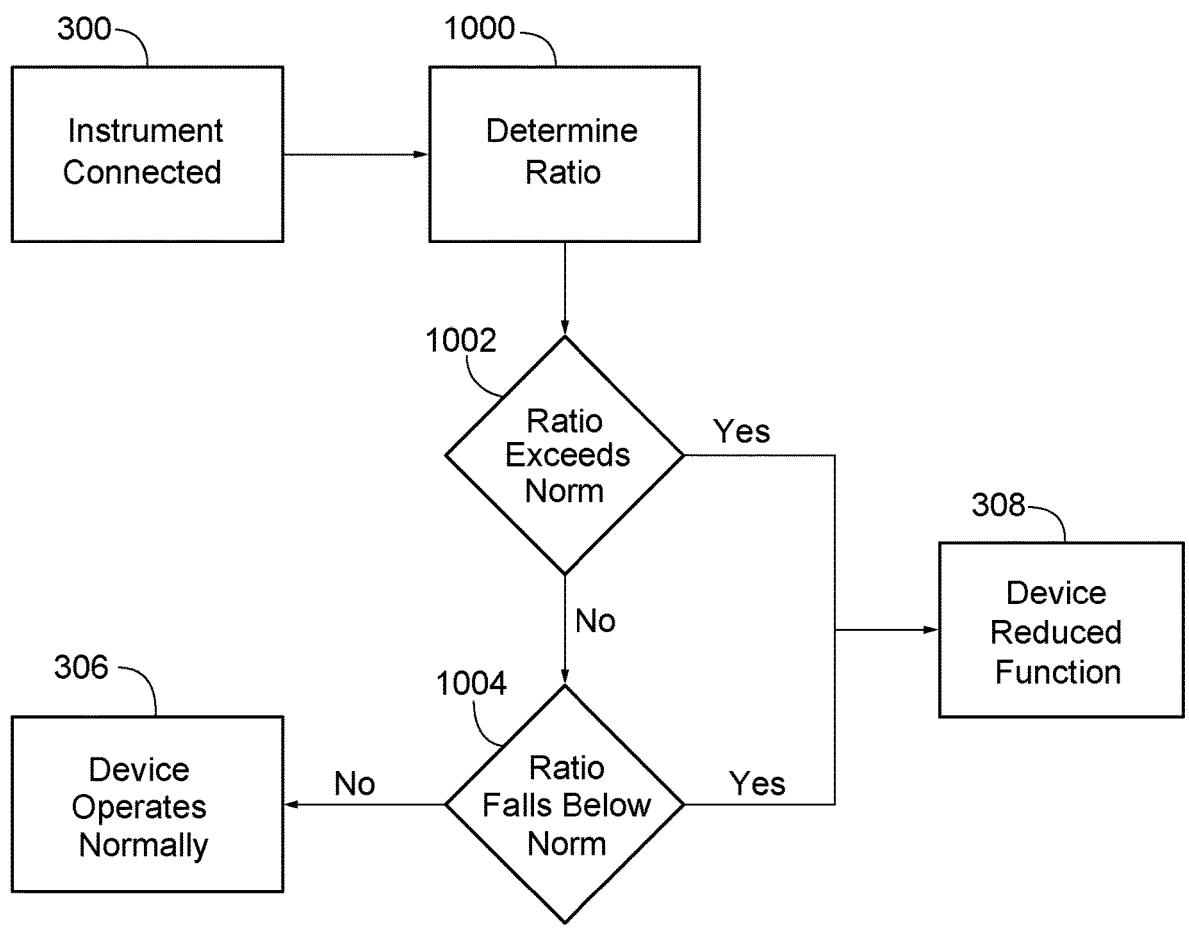
FIG. 10 depicts a flow chart showing an exemplary set of steps that may be performed to enforce device life limitations based upon a device usage ratio.

FIG. 10 shows an exemplary set of steps that could be performed to determine a ratio of instrument (100) usage to instrument (100) connection time in order to prevent circumvention of instrument (100) life management features. Information that is readily available to generator (122) and instrument (100) during operation includes the amount of total time a particular instrument (100) spends connected to a particular generator (122), the number of times an instrument (100) is activated, the total amount of time an instrument (100) is activated, average power generated by instrument (100), average current drawn by instrument (100), activation types, activation durations, and/or other similar information. Such readily available information can be examined for characteristics that strongly suggest abnormal use or attempts to circumvent instrument (100) usage safeguards.

When an instrument (100) is connected (block 300) to a generator (122), generator (122), or instrument (100), or both may examine EEPROM (150) or memory and retrieve instrument (100) usage information such as total connected time, total activation time, total activations, and similar instrument (100) usage so that one or more usage ratios may be determined (block 1000). A usage ratio might be total connected time relative to total activation time. Normal usage might indicate that during a ten-hour procedure instrument (100) is plugged in for 10 hours, and activated for 1 hour, so a usage ratio within the norm might be about 10:1. If the determined ratio exceeds this norm (block 1002) or falls below this norm (block 1004) by a substantial difference, instrument (100) may be placed into a state of reduced or disabled operation (block 308) by modifying EEPROM (150) of instrument (100). If the determined ratio (block 1000) is comparable to the expected ratio, instrument (100) may operate normally (block 306).

While FIG. 10 shows that a ratio may be tested for both exceeding a normal value 1002) as well as falling below a normal value (block 1004), it should be understood that in some versions a ratio may only be evaluated against one criteria. For example, in some versions a ratio may only be examined to determine if it exceeds a normal value (block 1002) before determining whether it will operate normally (block 306) or at a reduced function (block 308). Similarly, in other versions, a ratio may only be examined to determine if it falls short of a normal value (block 1004) before determining whether it will operate normally (block 306) or at a reduced function (block 308).

This instrument (100) life management feature may be useful where, for example, a user attempts to circumvent instrument (100) use limitations by keeping instrument (100) connected to generator (122) indefinitely in the hopes to avoid usage checks that only occur during connection and disconnection between instrument (100) and generator (122). As a result, instrument (100) may exhibit a ratio of 100 hours of connection time to 1 hour of use time, with the 100:1 ratio far exceeding the expected 10:1 ratio. This instrument (100) life management is also useful where, for example, a user attempts to circumvent instrument (100) use limitations on total use and generator (122) pairing by connecting an instrument (100), using instrument (100) briefly, and then disconnecting instrument (100), in order to prevent lockout or generator pairing (122) due to total connected time exceeding a threshold. An instrument (100) used in this way might exhibit a ratio of 10 hours of connected time to 9 hours of use time or activated time, a 10:9 ratio that falls short of the expected 10:1 ratio. Finer control could be achieved by storing a ratio matrix on the generator (122), where the acceptable ratio or range of ratios is also determined by the number of times an instrument (100) has been connected to a generator (122), with additional connections resulting in a narrow range of ratios that are considered normal use.

VII. Modifying Device Characteristics on Power Loss

One way that users may attempt to circumvent instrument (100) life management features is to minimize the amount of time that an instrument (100) is connected to a generator (122), in order to prevent generator (122) pairing. By connecting an instrument (100) to generator (122), using instrument (100) briefly, and then disconnecting instrument (100), instrument (100) and generator (122) are limited in their ability to determine the passage of time between a recent connection and a subsequent connection unless they are able to persistently track time despite without an external power source. However, a user in some cases has a legitimate need to disconnect and reconnect an instrument (100), such as when an error occurs, a different instrument is needed, an instrument needs mid-procedure cleaning, or the like. This means that it is not feasible to disable or partially disable an instrument (100) in every situation where one or more connections occur. One way to allow the user to cycle an instrument (100) connection when legitimate reasons exist for such an action is to detect generator (122) and instrument (100) errors and prevent an instrument (100) disconnection that occurs immediately after a generator or instrument error from being considered by instrument (100) life management features for the purpose of limiting subsequent use of instrument (100). For example, if a particular instrument (100) and generator (122) are configured to disable instrument (100) after 10 connections, a disconnection and reconnection that occurs within five minutes of a generator (122) or instrument (100) error may not be counted against this total.

Another method of providing some flexibility between usability and enforcement of safety mechanisms would be to enforce an instrument (100) half-life that is triggered by disconnection of instrument (100) from generator (122); or by generator (122) being powered down. This recognizes a need to occasionally shut down a generator (122) or disconnect instrument (100) from generator (122) during a procedure, such as for cleaning, repositioning of equipment or personnel, a patient emergency, or the like, while also maintaining some enforcement of safety mechanisms and instrument (100) life management principles.

Figure 11:
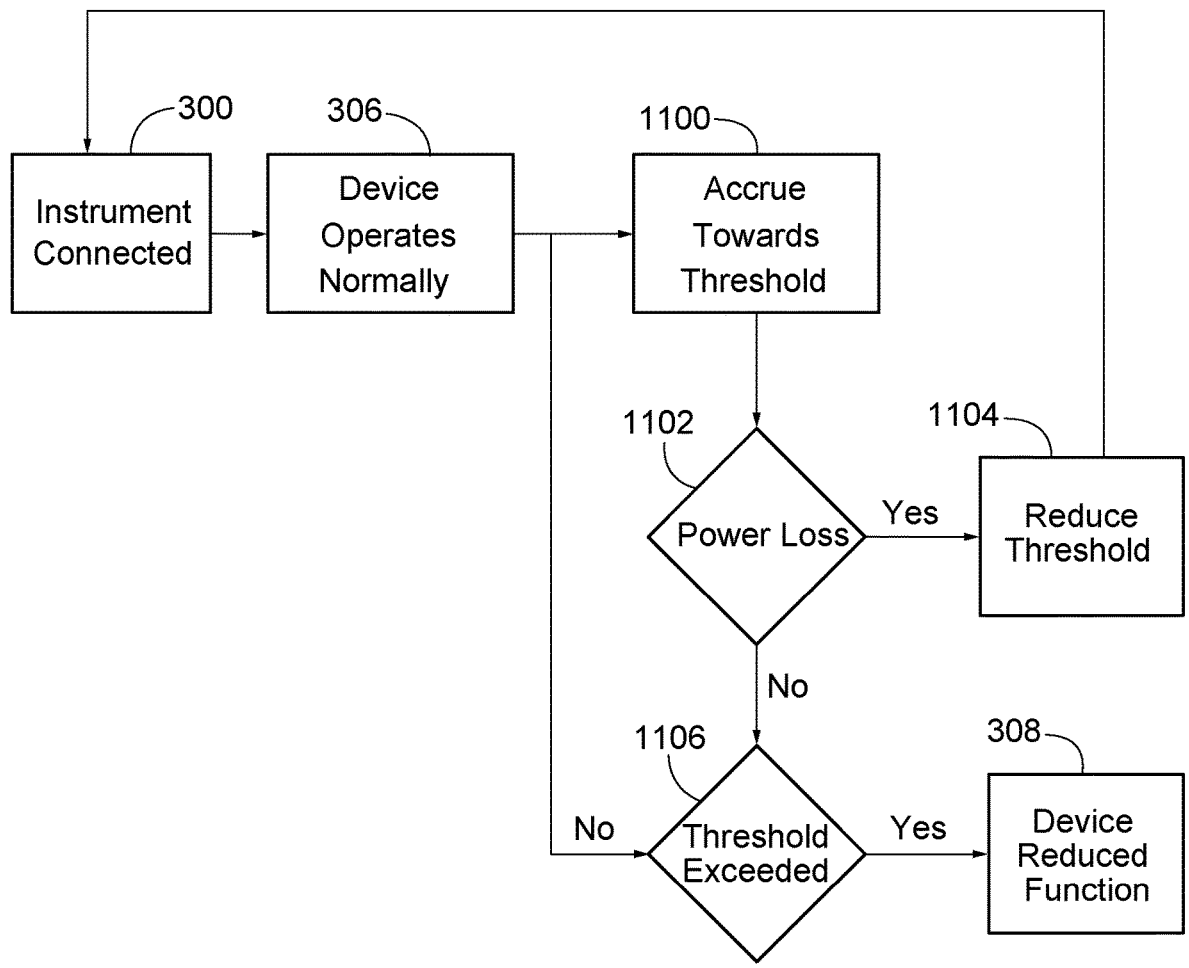
FIG. 11 depicts a flow chart showing an exemplary set of steps that may be performed to enforce a device half-life based upon reconnections.

FIG. 11 shows an exemplary set of steps that may be performed to enforce an instrument (TOO) half-life based upon reconnections. When an instrument (100) is connected (block 300), it would operate normally (block 306) and generator (122) or instrument (100) or both would begin to accrue time (block 1100) toward a connected time threshold that indicates the total time that instrument (100) has spent connected to generator (122). When exceeded, this connected time threshold may cause instrument (100) and generator (122) to be generator (122) paired, or may cause instrument (100) to be disabled entirely due to a total connected time limitation. If instrument (100) is used as would be expected during a normal procedure, there will be no power loss (block 1102) for instrument (100) or generator (122), and instrument (100) will eventually exceed a total time connected limitation (block 1106) and be placed into a fully disabled or partially disabled mode (block 308). However, with instrument (100) half-life triggered upon reconnection, in the event of a power loss (block 1102), the threshold for generator (122) pairing or total connected time will be reduced (block 1104) and enforced when instrument (100) is reconnected (block 300).

For example, if an instrument (100) is configured for ten hours of connected time for safety reasons, instrument (100) will be disabled after being connected to a generator (122) for a total of ten hours. If this instrument (100) loses power or generator (122) loses power before this ten-hour connection time is reached, the ten-hour threshold may be reduced (block 1104) in order to provide some flexibility to the user while preventing indefinite circumvention of the total time connected limitation. As an example, if the threshold for total time connected is ten hours before instrument (100) is deactivated, and instrument (100) is connected for 1 hour and then disconnected from generator (122), the threshold may be reduced to 7.5 hours or 5 hours upon reconnection between instrument (100) and generator (122). If instrument (100) is subsequently disconnected from generator (122) and reconnected with generator (122), the threshold may be reduced (block 1104) again to 5 hours, or 2.5 hours. In this manner, if a user attempts to overuse instrument (100) and circumvent limitations by constant disconnection and reconnection from/with generator (122), instrument (100) usage threshold will be reduced to a point where even the minimized usage causes instrument (100) to be disabled before extreme overuse can occur. This technique may be combined with other techniques, such as ignoring reconnections after an error, or ignoring a disconnection and reconnection if limited activation of instrument (100) suggests that instrument (100) was only briefly plugged in to test that instrument (100) will activate during a medical procedure, in order to reduce negative impact on legitimate uses of instrument (100).

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising a surgical instrument, the surgical instrument comprising a generator connection, a user input, a processor, and a memory, wherein the memory is configured to store a set of device life management characteristics, wherein the processor is configured to enable or disable the surgical instrument based upon the set of device life management characteristics.

EXAMPLE 2

The apparatus of Example 1, wherein the surgical instrument further comprises a timing battery circuit, wherein the timing battery circuit is in communication with the processor such that the processor is configured to disable at least a portion of the surgical instrument based on a signal from the timing battery circuit.

EXAMPLE 3

The apparatus of Example 2, wherein the timing battery circuit comprises a battery, a discharge load feature, and an activation switch, wherein the generator connection is configured to close the activation switch when the surgical instrument is connected to a generator.

EXAMPLE 4

The apparatus of Example 3, wherein the discharge load feature is configured to discharge the battery at a predetermined discharge rate.

EXAMPLE 5

The apparatus of Example 4, wherein the processor is further configured to disable the surgical instrument when the battery charge falls below an activation threshold.

EXAMPLE 6

The apparatus of any one or more of Examples 4 through 5, wherein the predetermined discharge rate is selected to result in the battery charge falling below the activation threshold after the battery is coupled with the discharge load feature for between about 4 hours and about 24 hours.

EXAMPLE 7

The apparatus of any one or more of Examples 3 through 6, wherein the discharge load feature comprises a resistor.

EXAMPLE 8

The apparatus of any one or more of Examples 1 through 7, wherein the surgical instrument further comprises a timing circuit, wherein the timing circuit comprises a capacitor and a discharge load feature.

EXAMPLE 9

The apparatus of Example 8, wherein the generator connection is configured to supply power to the timing circuit and charge the capacitor to an initial charge when the surgical instrument is connected to a generator

EXAMPLE 10

The apparatus of Example 9, wherein the discharge load feature is configured to provide a predetermined discharge rate for the capacitor.

EXAMPLE 11

The apparatus of Example 10, wherein the processor is further configured to disable the surgical instrument when the capacitor charge falls below an activation threshold.

EXAMPLE 12

The apparatus of Example 11, the memory is configured to receive a charge bit is in response to the capacitor reaching the initial charge.

EXAMPLE 13

The apparatus of Example 12, wherein the processor is further configured to cease charging the capacitor when the charge bit is present on the memory.

EXAMPLE 14

The apparatus of any one or more of Examples 10 through 13, wherein the predetermined discharge rate for the capacitor is selected to result in the capacitor charge falling below the activation threshold after the capacitor is coupled with the discharge load feature for between about 4 hours and about 24 hours.

EXAMPLE 15

The apparatus of any one or more of Examples 1 through 14, further comprising a generator, the generator comprising a display and a user input, wherein the generator is configured to store a list of unique identifiers, wherein each unique identifier is associated with a used surgical instrument.

EXAMPLE 16

The apparatus of Example 15, wherein the generator is configured to operate the surgical instrument at a reduced functionality when the surgical instrument is represented on the list of unique identifiers.

EXAMPLE 17

The apparatus of any one or more of Examples 15 through 16, wherein the generator is configured to prevent the surgical instrument from being added to the list of unique identifiers when the surgical instrument is disconnected from the generator as a result of a generator error.

EXAMPLE 18

The apparatus of any one or more of Examples 15 through 17, wherein the generator is configured to add the surgical instrument to the list of unique identifiers when the surgical instrument is disconnected from the generator as a result of a generator power loss.

EXAMPLE 19

The apparatus of any one or more of Examples 15 through 18, wherein the generator is configured to add the surgical instrument to the list of unique identifiers in response to receiving an indication via the user input that a use of surgical instrument is complete.

EXAMPLE 20

The apparatus of any one or more of Examples 1 through 19, further comprising a generator and an external timer, wherein the external timer is configured to maintain a present time indicator.

EXAMPLE 21

The apparatus of Example: 20, wherein the external timer comprises a timer processor, a timer memory, and a battery.

EXAMPLE 22

The apparatus of Example 21, wherein the generator is configured to charge the battery.

EXAMPLE 23

The apparatus of any one or more of Examples 20 through 22, wherein the generator is operable to retrieve the present time indicator from the external timer and write the present time indicator to a generator memory.

EXAMPLE 24

The apparatus of Example 23, wherein the generator is further configured to associate the surgical instrument with the present time indicator when the surgical instrument is connected to the generator.

EXAMPLE 25

The apparatus of Example 24, wherein the generator is configured to operate the surgical instrument at a reduced functionality when two or more present time indicators associated with the surgical instrument indicate that the surgical instrument has exceeded a usable life.

EXAMPLE 26

The apparatus of Example 25, wherein the usable life is between about 4 and about 24 hours.

EXAMPLE 27

The apparatus of any one or more of Examples 1 through 26, wherein the processor is configured to determine a total generator connection time from the set of device life management characteristics, wherein the total generator connection time indicates a total duration of time that the surgical instrument has been connected to a generator.

EXAMPLE 28

The apparatus of Example 27, wherein the processor is configured to determine a total activation time from the set of device life management characteristics, wherein the total activation time indicates the total duration of time that the surgical instrument has been activated.

EXAMPLE 29

The apparatus of Example 28, wherein the processor is configured to determine a ratio of the total generator connection time to the total activation time.

EXAMPLE 30

The apparatus of Example 29, wherein the processor is configured to operate the surgical instrument at a reduced functionality when the ratio exceeds an upper abnormal use threshold or when the ratio falls short of a lower abnormal use threshold.

EXAMPLE 31

The apparatus of any one or more of Examples 1 through 30, wherein the processor is configured to determine a total generator connection time from the device life management characteristics, wherein the total generator connection time indicates the duration of time that the surgical instrument has been connected to a generator.

EXAMPLE 32

The apparatus of Example 31, wherein the processor is configured to operate the surgical instrument at a reduced functionality when the total generator connection time exceeds a connection threshold.

EXAMPLE 33

The apparatus of any one or more of Examples 31 through 32, wherein the processor is configured to reduce the connection threshold each time the surgical instrument is disconnected from the generator.

EXAMPLE 34

The apparatus of Example 33, wherein the connection threshold is about 12 hours, and wherein the processor is configured to reduce the connection threshold to about 6

EXAMPLE 35

An apparatus comprising a surgical instrument, the surgical instrument comprising: an end effector, wherein the end effector comprises a surgical feature, a generator connection, a user input, wherein the user input is operable to activate the surgical feature of the end effector, a processor, and a memory, wherein the memory is configured to store a set of device life management characteristics, and wherein the processor is configured to enable or disable the surgical feature based upon the set of device life management characteristics.

EXAMPLE 36

The apparatus of Example 35, wherein the surgical instrument further comprises a timing battery circuit, and wherein the processor is configured to disable the surgical feature based on a signal from the timing battery circuit.

EXAMPLE 37

The apparatus of Example 36, wherein the timing battery circuit comprises a battery, a discharge load feature, and an activation switch, wherein the generator connection is configured to close the activation switch when the surgical instrument is connected to a generator.

EXAMPLE 38

The apparatus of Example 37, wherein the discharge load feature comprises a resistor configured to discharge the battery at a predetermined discharge rate.

EXAMPLE 39

The apparatus of Example 38, wherein the processor is further configured to disable the surgical feature when the battery charge falls below a disable threshold, wherein the predetermined discharge rate is selected to result in the battery charge falling below the disable threshold between about 4 hours and about 24 hours after the activation switch is closed.

EXAMPLE 40

The apparatus of any one or more of Examples 37 through 39, wherein the discharge load feature comprises a light emitting diode configured to discharge the battery at a predetermined discharge rate.

EXAMPLE 41

The apparatus of any one or more of Examples 36 through 40, further comprising a timing circuit, wherein the timing circuit comprises a capacitor and a discharge load feature.

EXAMPLE 42

The apparatus of Example 41, wherein the generator connection is configured to supply power to the timing circuit and charge the capacitor to an initial charge when the surgical instrumented is connected to a generator.

EXAMPLE 43

The apparatus of Example 42, wherein the discharge load feature is configured to provide a predetermined discharge rate for the capacitor, and wherein the surgical feature is disabled when the capacitor charge falls below a disable threshold.

EXAMPLE 44

The apparatus of Example 43, wherein the memory is configured to receive a charge bit in response to the capacitor reaching the initial charge, and wherein the processor is further configured to cease charging the capacitor when the charge bit is present on the memory.

EXAMPLE 45

The apparatus of any one or more of Examples 35 through 44, further comprising a generator, the generator comprising: a display, and a generator user input, wherein the generator is configured to store a list of unique identifiers, wherein each unique identifier is associated with a used surgical instrument, and wherein the generator is configured to disable the surgical feature when the surgical instrument is represented in the list of unique identifiers.

EXAMPLE 46

The apparatus of Example 45, wherein the generator is configured to prevent the surgical instrument from being added to the list of unique identifiers when the surgical instrument is disconnected from the generator as a result of a generator error.

EXAMPLE 47

The apparatus of any one or more of Examples 45 through 46, wherein the generator is configured to add the surgical instrument to the list of unique identifiers when the surgical instrument disconnected from the generator as a result of a generator power loss.

EXAMPLE 48

The apparatus of any one or more of Examples 45 through 47, wherein the generator is configured to add the surgical instrument to the list of unique identifiers in response to receiving an indication via the generator user input that a use of the surgical instrument is complete.

EXAMPLE 49

The apparatus of any one or more of Examples 35 through 48, further comprising a generator, comprising a generator memory; and an external timer, comprising a timer processor, a timer memory, and a battery, wherein the external timer is configured to maintain a present time indicator, and wherein the generator is configured to charge the battery, retrieve the present time indicator from the external timer and write the present time indicator to the generator memory, associate the surgical instrument with the present time indicator when the surgical instrument is connected to the generator, and the surgical feature when two or more hours after a first disconnection, to about 3 hours after a second disconnection, and to about 1.5 hours after a third disconnection.

present time indicators associated with the surgical instrument indicate that the surgical instrument has exceeded a usable life.

EXAMPLE 50

The apparatus of any one or more of Examples 35 through 49, wherein the processor is configured to determine a total generator connection time based upon the set of device life management characteristics, wherein the total generator connection time indicates a total duration of time that the surgical instrument has been connected to a generator, determine a total activation time based upon the set of device life management characteristics, wherein the total activation time indicates the total duration of time that the end effector has been in use, determine a usage ratio of the total generator connection time to the total activation time, and disable the surgical feature when the usage ratio exceeds an upper abnormal use threshold or when the ratio falls short of a lower abnormal use threshold.

EXAMPLE 51

The apparatus of any one or more of Examples 35 through 50, wherein the processor is configured to determine a total generator connection time based upon the device life management characteristics, wherein the total generator connection time indicates the duration of time that the surgical instrument has been connected to a generator, disable the surgical feature when the total generator connection time exceeds a connection time threshold, and reduce the connection time threshold each time the surgical instrument is disconnected from the generator.

EXAMPLE 52

The apparatus of Example 51, wherein the connection threshold is about 12 hours, and wherein the processor is configured to reduce the connection threshold to about 6 hours after a first disconnection from the generator, to about 3 hours after a second disconnection from the generator, and to about 1.5 hours after a third disconnection from the generator.

EXAMPLE 53

An apparatus comprising: a surgical instrument, the surgical instrument comprising: an end effector, wherein the end effector comprises a surgical feature, a generator connection, a user input, wherein the user input is operable to activate the surgical feature of the end effector, a processor, and a memory, wherein the memory is configured to store a set of device life management characteristics, wherein the processor is configured to enable or disable at the surgical feature based upon the set of device life management characteristics; and a generator, the generator comprising: a display, and a generator user input, wherein the generator is configured to store a list of unique identifiers, wherein each unique identifier is associated with a used surgical instrument, and wherein the generator is configured to disable the surgical feature when the surgical instrument is represented in the list of unique identifiers, wherein the generator is configured to: prevent the surgical instrument from being added to the list of unique identifiers when the surgical instrument is disconnected from the generator as a result of a generator error, add the surgical instrument to the list of unique identifiers when the surgical instrument disconnected from the generator as a result of a generator power loss, and add the surgical instrument to the list of unique identifiers in response to receiving an indication via the generator user input that a use of the surgical instrument is complete.

EXAMPLE 54

An apparatus comprising a surgical instrument, the surgical instrument comprising: an end effector, wherein the end effector comprises a surgical feature, a generator connection, a user input, wherein the user input is operable to activate the surgical feature of the end effector, a processor, and a memory, wherein the memory is configured to store a set of device life management characteristics, and wherein the processor is configured to enable or disable the surgical feature based upon the set of device life management characteristics, wherein the processor is further configured to: determine a total generator connection time based upon the set of device life management characteristics, wherein the total generator connection time indicates a total duration of time that the surgical instrument has been connected to a generator, determine a total activation time based upon the set of device life management characteristics, wherein the total activation time indicates the total duration of time that the end effector has been in use, determine a usage ratio of the total generator connection time to the total activation time, disable the surgical feature when the usage ratio exceeds an upper abnormal use threshold or when the ratio falls short of a lower abnormal use threshold, disable the surgical when the total generator connection time exceeds a connection time threshold, and reduce the connection time threshold each time the surgical instrument is disconnected from the generator.

IX. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to he incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising a surgical instrument, the surgical instrument comprising:
   (i) an end effector, wherein the end effector comprises a surgical feature,
   (ii) a generator connection,
   (iii) a user input, wherein the user input is operable to activate the surgical feature of the end effector,
   (iv) a processor,
   (v) a timer feature configured to generate a value signal that changes at a predetermined rate, and
   (vi) a memory, wherein the memory is configured to store a set of device life management characteristics, wherein at least one of the device life management characteristics is based at least in part on the value signal from the timer feature, and
   wherein the processor is configured to enable or disable the surgical feature based upon the set of device life management characteristics.

2. The apparatus of claim 1, wherein the timer feature further includes a timing battery circuit, and wherein the processor is configured to disable the surgical feature based on a signal from the timing battery circuit.

3. The apparatus of claim 2, wherein the timing battery circuit comprises a battery, a discharge load feature, and an activation switch, wherein the generator connection is configured to close the activation switch when the surgical instrument is connected to a generator.

4. The apparatus of claim 3, wherein the discharge load feature comprises a resistor configured to discharge the battery at a predetermined discharge rate.

5. The apparatus of claim 4, wherein the processor is further configured to disable the surgical feature when the battery charge falls below a disable threshold, wherein the predetermined discharge rate is selected to result in the battery charge falling below the disable threshold between about 4 hours and about 24 hours after the activation switch is closed.

6. The apparatus of claim 3, wherein the discharge load feature comprises a light emitting diode configured to discharge the battery at a predetermined discharge rate.

7. The apparatus of claim 1, wherein the timer feature further includes a timing circuit, wherein the timing circuit comprises a capacitor and a discharge load feature.

8. The apparatus of claim 7, wherein the generator connection is configured to supply power to the timing circuit and charge the capacitor to an initial charge when the surgical instrumented is connected to a generator.

9. The apparatus of claim 8, wherein the discharge load feature is configured to provide a predetermined discharge rate for the capacitor, and wherein the surgical feature is disabled when the capacitor charge falls below a disable threshold.

10. The apparatus of claim 9, wherein the memory is configured to receive a charge bit in response to the capacitor reaching the initial charge, and wherein the processor is further configured to cease charging the capacitor when the charge bit is present on the memory.

11. The apparatus of claim 1, further comprising a generator, the generator comprising:
    (i) a display, and
    (ii) a generator user input, wherein the generator is configured to store a list of unique identifiers,
    wherein each unique identifier is associated with a used surgical instrument, and
    wherein the generator is configured to disable the surgical feature when the surgical instrument is represented in the list of unique identifiers.

12. The apparatus of claim 11, wherein the generator is configured to prevent the surgical instrument from being added to the list of unique identifiers when the surgical instrument is disconnected from the generator as a result of a generator error.

13. The apparatus of claim 11, wherein the generator is configured to add the surgical instrument to the list of unique identifiers when the surgical instrument disconnected from the generator as a result of a generator power loss.

14. The apparatus of claim 11, wherein the generator is configured to add the surgical instrument to the list of unique identifiers in response to receiving an indication via the generator user input that a use of the surgical instrument is complete.

15. The apparatus of claim 1, further comprising:
(a) a generator, comprising a generator memory; and
(b) an external timer, comprising a timer processor, a timer memory, and a battery,
wherein the external timer is configured to maintain a present time indicator, and
wherein the generator is configured to:
(i) charge the battery,
(ii) retrieve the present time indicator from the external timer and write the present time indicator to the generator memory,
(iii) associate the surgical instrument with the present time indicator when the surgical instrument is connected to the generator, and
(iv) disable the surgical feature when two or more present time indicators associated with the surgical instrument indicate that the surgical instrument has exceeded a usable life.

16. The apparatus of claim 1, wherein the processor is configured to:
(A) determine a total generator connection time based upon the set of device life management characteristics, wherein the total generator connection time indicates a total duration of time that the surgical instrument has been connected to a generator,
(B) determine a total activation time based upon the set of device life management characteristics, wherein the total activation time indicates the total duration of time that the end effector has been in use,
(C) determine a usage ratio of the total generator connection time to the total activation time, and
(D) disable the surgical feature when the usage ratio exceeds an upper abnormal use threshold or when the ratio falls short of a lower abnormal use threshold.

17. The apparatus of claim 1, wherein the processor is configured to:
(A) determine a total generator connection time based upon the device life management characteristics, wherein the total generator connection time indicates the duration of time that the surgical instrument has been connected to a generator,
(B) disable the surgical feature when the total generator connection time exceeds a connection time threshold, and
(C) reduce the connection time threshold each time the surgical instrument is disconnected from the generator.

18. The apparatus of claim 17, wherein the connection threshold is about 12 hours, and wherein the processor is configured to reduce the connection threshold to about 6 hours after a first disconnection from the generator, to about 3 hours after a second disconnection from the generator, and to about 1.5 hours after a third disconnection from the generator.

19. An apparatus, comprising:
(a) a surgical instrument, the surgical instrument comprising:
(i) an end effector, wherein the end effector comprises a surgical feature,
(ii) a generator connection,
(iii) a user input, wherein the user input is operable to activate the surgical feature of the end effector,
(iv) a processor,
(v) a memory, wherein the memory is configured to store a set of device life management characteristics, and
wherein the processor is configured to enable or disable the surgical feature based upon the set of device life management characteristics; and
(b) a generator, comprising:
(i) a display, and
(ii) a generator user input, wherein the generator is configured to store a list of unique identifiers,
wherein each unique identifier is associated with a used surgical instrument, and
wherein the generator is configured to disable the surgical feature when the surgical instrument is represented in the list of unique identifiers.

20. An apparatus, comprising:
(a) a surgical instrument, the surgical instrument comprising:
(i) an end effector, wherein the end effector comprises a surgical feature,
(ii) a generator connection,
(iii) a user input, wherein the user input is operable to activate the surgical feature of the end effector,
(iv) a processor,
(v) a memory, wherein the memory is configured to store a set of device life management characteristics, and
wherein the processor is configured to enable or disable the surgical feature based upon the set of device life management characteristics;
(b) a generator, comprising a generator memory; and
(c) an external timer, comprising a timer processor, a timer memory, and a battery, wherein the external timer is configured to maintain a present time indicator, and
wherein the generator is configured to:
(i) charge the battery,
(ii) retrieve the present time indicator from the external timer and write the present time indicator to the generator memory,
(iii) associate the surgical instrument with the present time indicator when the surgical instrument is connected to the generator, and
(iv) disable the surgical feature when two or more present time indicators associated with the surgical instrument indicate that the surgical instrument has exceeded a usable life.

* * * * *